(12) United States Patent
Ward et al.

(10) Patent No.: US 8,366,999 B2
(45) Date of Patent: Feb. 5, 2013

(54) NANOTUBE FABRIC-BASED SENSOR SYSTEMS AND METHODS OF MAKING SAME

(75) Inventors: Jonathan W. Ward, Fairfax, VA (US); Brent M. Segal, Woburn, MA (US)

(73) Assignee: Nantero Inc., Woburn, MA (US)

( * ) Notice: Subject to any disclaimer, the term of this patent is extended or adjusted under 35 U.S.C. 154(b) by 546 days.

(21) Appl. No.: 12/065,857

(22) PCT Filed: Sep. 6, 2006

(86) PCT No.: PCT/US2006/034627
§ 371 (c)(1),
(2), (4) Date: Sep. 23, 2008

(87) PCT Pub. No.: WO2007/030484
PCT Pub. Date: Mar. 15, 2007

(65) Prior Publication Data
US 2009/0140167 A1    Jun. 4, 2009

Related U.S. Application Data

(60) Provisional application No. 60/714,388, filed on Sep. 6, 2005.

(51) Int. Cl.
*G01N 21/00* (2006.01)
*H01L 27/14* (2006.01)

(52) U.S. Cl. .................................... 422/82.05; 257/414

(58) Field of Classification Search ............... 422/82.05; 257/414
See application file for complete search history.

(56) References Cited

U.S. PATENT DOCUMENTS

| | | | |
|---|---|---|---|
| 6,057,637 A | 5/2000 | Zettl et al. | |
| 6,187,823 B1 | 2/2001 | Haddon et al. | |
| 6,277,318 B1 | 8/2001 | Bower et al. | |
| 6,331,262 B1 | 12/2001 | Haddon et al. | |
| 6,342,276 B1 | 1/2002 | You et al. | |
| 6,361,958 B1 | 3/2002 | Shieh | |
| 6,368,569 B1 | 4/2002 | Haddon et al. | |
| 6,409,567 B1 | 6/2002 | Amey, Jr. et al. | |
| 6,423,583 B1 | 7/2002 | Avouris et al. | |
| 6,495,116 B1 | 12/2002 | Herman | |
| 6,495,258 B1 | 12/2002 | Chen et al. | |
| 6,515,339 B2 | 2/2003 | Shin et al. | |

(Continued)

FOREIGN PATENT DOCUMENTS

| | | |
|---|---|---|
| EP | 0947466 | 10/1999 |
| EP | 1061040 | 12/2000 |

(Continued)

OTHER PUBLICATIONS

Ago, H. et al., "Workfunction of Purified and Oxidised Carbon Nanotubes," Synthetic Metals 103 (1999) 2494-2495.

(Continued)

*Primary Examiner* — Lore Jarrett
(74) *Attorney, Agent, or Firm* — Nantero Inc.

(57) ABSTRACT

Under one aspect, a system (100) for sensing the presense of an analyte in a fluid includes a nanotube sensor element including a plurality of nanotubes and positioned for exposure to a fluid; an optical source capable of generating optical radiation (102), the radiation having a source frequency and a fluence selected to generate a nonlinear optical response by the nanotube sensor element; an optical detector (110) capable of measuring the nonlinear optical response by the nanotube sensor element; and logic in electrical communications with the optical detector to sense the presense of an analyte in the fluid based on the nonlinear optical response measured by the optical detector.

28 Claims, 15 Drawing Sheets

U.S. PATENT DOCUMENTS

| | | | |
|---|---|---|---|
| 6,528,020 | B1 | 3/2003 | Dai et al. |
| 6,531,513 | B2 | 3/2003 | Haddon et al. |
| 6,548,313 | B1 | 4/2003 | Ravi et al. |
| 6,574,130 | B2 | 6/2003 | Segal et al. |
| 6,630,772 | B1 | 10/2003 | Bower et al. |
| 6,641,793 | B2 | 11/2003 | Haddon et al. |
| 6,643,165 | B2 | 11/2003 | Segal et al. |
| 6,645,628 | B2 | 11/2003 | Shiffler, Jr. et al. |
| 6,706,402 | B2 | 3/2004 | Rueckes et al. |
| 6,707,098 | B2 | 3/2004 | Hofmann et al. |
| 6,752,977 | B2 | 6/2004 | Smalley et al. |
| 6,784,028 | B2 | 8/2004 | Rueckes et al. |
| 6,808,746 | B1 | 10/2004 | Dai et al. |
| 6,833,558 | B2 | 12/2004 | Lee et al. |
| 6,835,591 | B2 | 12/2004 | Rueckes et al. |
| 6,858,197 | B1 | 2/2005 | Delzeit |
| 6,863,942 | B2 | 3/2005 | Ren et al. |
| 6,896,864 | B2 | 5/2005 | Clarke |
| 6,899,945 | B2 | 5/2005 | Smalley et al. |
| 6,911,682 | B2 | 6/2005 | Rueckes et al. |
| 6,918,284 | B2 | 7/2005 | Snow et al. |
| 6,919,592 | B2 | 7/2005 | Segal et al. |
| 6,919,740 | B2 | 7/2005 | Snider |
| 6,921,575 | B2 | 7/2005 | Horiuchi et al. |
| 6,924,538 | B2 | 8/2005 | Jaiprakash et al. |
| 6,946,410 | B2 | 9/2005 | French et al. |
| 6,990,009 | B2 | 1/2006 | Bertin et al. |
| 7,057,402 | B2 | 6/2006 | Cole et al. |
| 7,097,906 | B2 | 8/2006 | Gardner |
| 7,115,864 | B2 | 10/2006 | Colbert et al. |
| 7,115,960 | B2 | 10/2006 | Bertin |
| 7,118,440 | B2 | 10/2006 | Kuo et al. |
| 7,176,505 | B2 | 2/2007 | Rueckes et al. |
| 7,259,410 | B2 | 8/2007 | Jaiprakash et al. |
| 7,335,395 | B2 | 2/2008 | Ward et al. |
| 7,348,298 | B2 | 3/2008 | Zhang et al. |
| 7,416,993 | B2 | 8/2008 | Segal et al. |
| 7,538,400 | B2 | 5/2009 | Segal et al. |
| 7,566,478 | B2 | 7/2009 | Ward et al. |
| 7,780,918 | B2 | 8/2010 | Segal et al. |
| 7,786,540 | B2 | 8/2010 | Segal et al. |
| 7,835,266 | B2 | 11/2010 | Kumano et al. |
| 2001/0004979 | A1 | 6/2001 | Han et al. |
| 2002/0081380 | A1 | 6/2002 | Dillon et al. |
| 2002/0160111 | A1 | 10/2002 | Sun et al. |
| 2002/0172963 | A1 | 11/2002 | Kelley |
| 2002/0179434 | A1 | 12/2002 | Dai |
| 2003/0004058 | A1 | 1/2003 | Li et al. |
| 2003/0065206 | A1 | 4/2003 | Bolskar et al. |
| 2003/0089899 | A1* | 5/2003 | Lieber et al. ............ 257/9 |
| 2003/0122111 | A1 | 7/2003 | Glatkowski |
| 2003/0177450 | A1 | 9/2003 | Nugent |
| 2003/0200521 | A1 | 10/2003 | DeHon et al. |
| 2003/0220518 | A1 | 11/2003 | Bolskar et al. |
| 2004/0005723 | A1 | 1/2004 | Empedocles et al. |
| 2004/0007528 | A1 | 1/2004 | Bakajin et al. |
| 2004/0023253 | A1 | 2/2004 | Kunwar et al. |
| 2004/0023514 | A1 | 2/2004 | Moriya et al. |
| 2004/0029706 | A1 | 2/2004 | Barrera et al. |
| 2004/0031975 | A1 | 2/2004 | Kern et al. |
| 2004/0034177 | A1 | 2/2004 | Chen |
| 2004/0041154 | A1 | 3/2004 | Watanabe et al. |
| 2004/0043527 | A1 | 3/2004 | Bradley et al. |
| 2004/0058153 | A1 | 3/2004 | Ren et al. |
| 2004/0071949 | A1 | 4/2004 | Glatkowski et al. |
| 2004/0099438 | A1 | 5/2004 | Arthur et al. |
| 2004/0104129 | A1 | 6/2004 | Gu et al. |
| 2004/0147037 | A1 | 7/2004 | Dai et al. |
| 2004/0181630 | A1 | 9/2004 | Jaiprakash et al. |
| 2004/0253167 | A1 | 12/2004 | Silva et al. |
| 2004/0265550 | A1 | 12/2004 | Glatkowski et al. |
| 2005/0053525 | A1 | 3/2005 | Segal et al. |
| 2005/0058797 | A1 | 3/2005 | Sen et al. |
| 2005/0062035 | A1 | 3/2005 | Bertin et al. |
| 2005/0065741 | A1 | 3/2005 | Segal et al. |
| 2005/0095938 | A1 | 5/2005 | Rosenberger et al. |
| 2005/0128788 | A1 | 6/2005 | Segal et al. |
| 2005/0269554 | A1 | 12/2005 | Sen et al. |
| 2006/0052509 | A1 | 3/2006 | Saitoh |
| 2006/0061011 | A1 | 3/2006 | Kikuchi et al. |
| 2006/0146323 | A1 | 7/2006 | Bratkovski et al. |
| 2006/0204427 | A1 | 9/2006 | Ghenciu et al. |
| 2006/0237537 | A1 | 10/2006 | Empedocles et al. |
| 2006/0237805 | A1 | 10/2006 | Segal et al. |
| 2006/0276056 | A1 | 12/2006 | Ward et al. |
| 2007/0004191 | A1 | 1/2007 | Gu et al. |
| 2008/0153491 | A1 | 6/2008 | Cho et al. |
| 2010/0022045 | A1 | 1/2010 | Segal et al. |

FOREIGN PATENT DOCUMENTS

| | | |
|---|---|---|
| GB | 2 364 933 A | 2/2002 |
| JP | 2000203821 | 7/2000 |
| JP | 2001035362 A | 2/2001 |
| JP | 2004090208 A | 3/2004 |
| JP | 2005036112 A | 2/2005 |
| WO | WO-98/39250 A1 | 9/1998 |
| WO | WO-99/65821 A1 | 12/1999 |
| WO | WO-00/17101 | 3/2000 |
| WO | WO-00/62931 | 10/2000 |
| WO | WO-01/03208 A1 | 1/2001 |
| WO | WO-02/48701 A2 | 6/2002 |
| WO | WO-02/245113 A2 | 6/2002 |
| WO | WO-02/248701 A2 | 6/2002 |
| WO | WO-02/060812 A2 | 8/2002 |
| WO | WO-03/016901 A1 | 2/2003 |
| WO | WO-03/022733 A2 | 3/2003 |
| WO | WO-03/034142 A1 | 4/2003 |
| WO | WO-03/091486 A1 | 11/2003 |
| WO | WO-2004/003654 A1 | 1/2004 |
| WO | WO-2004/039893 A1 | 5/2004 |
| WO | WO-2004/065655 A1 | 8/2004 |
| WO | WO-2004/065657 A1 | 8/2004 |
| WO | WO-2004/065671 A1 | 8/2004 |
| WO | WO-2005/019793 | 3/2005 |
| WO | WO-2005/031299 | 4/2005 |
| WO | WO-2006/078293 A2 | 7/2006 |

OTHER PUBLICATIONS

Ajayan, P.M. et al., "Applications of Carbon Nanotubes," Topics Appl. Phys. 80, 391-425 (2001).

Ausman, K.D. et al., "Organic Solvent Dispersions of Single-Walled Carbon Nanotubes: Toward Solutions of Pristine Nanotubes," The Journal of Physical Chemistry B, vol. 104, No. 38, Sep. 28, 2000, 8911-8915.

Bahr, J.L. et al., "Dissolution of small diameter single-wall carbon nanotubes in organic solvents?" Chem. Commun., 2001, 193-194.

Banerjee, S. et al., "Functionalization of Carbon Nanotubes with a Metal-Containing Molecular Complex," Nano Letters, 2002, vol. 2, No. 1, 49-53.

Berhan, L. et al., "Mechanical properties of nanotube sheets: Alterations in joint morphology and achievable moduli in manufacturable materials," Journal of Applied Physics, vol. 95, No. 8, 4335-4345, Apr. 15, 2004.

Bonard, J. et al., "Monodisperse Multiwall Carbon Nanotubes Obtained with Ferritin as Catalyst," Nano Letters, 2002, vol. 2, No. 6, 665-667.

Cassell, A.M. et al., "Large Scale CVD Synthesis of Single-Walled Carbon Nanotubes," J. Phys. Chem. B 1999, 103, 6484-6492.

Chen, B. et al., "Heterogeneous Single-Walled Carbon Nanotube Catalyst Discovery and Optimization," Chem. Mater. 2002, 14, 1891-1896.

Chen, J. et al., "Dissolution of Full-Length Single-Walled Carbon Nanotubes," J. Phys. Chem. B, 2001, 105, 2525-2528.

Chen, J. et al., "Solution Properties of Single-Walled Carbon Nanotubes," Science, vol. 282, Oct. 2, 1998, 95-98.

Chen, R.J. et al., "Noncovalent Sidewall Functionalization of Single-Walled Carbon Nanotubes for Protein Immobilization," J. Am. Chem. Soc. 2001, 123, 3838-3839.

Cheng, H.M. et al., "Large-scale and low-cost synthesis of single-walled carbon nanotubes by the catalytic pyrolysis of hydrocarbons," Applied Physics Letters, vol. 72, No. 25, Jun. 22, 1998.

Chiang, I.W. et al., Purification and Characterization of Single-Wall Carbon Nanotubes (SWNTs) Obtained from the Gas-Phase Decomposition of CO (HiPco Process), J. Phys. Chem. B, 2001, 105, 8297-8301.

Chiang, I.W. et al., "Purification and Characterization of Single-Wall Carbon Nanotubes," J. Phys. Chem. B 2001, 105, 1157-1161.
Colomer, J.F. et al., "Different purification methods of carbon nanotubes produced by catalytic synthesis," Snythetic Metals 103 (1999) 2482-2483.
English Translation of the TIPO's Search Report for ROC Patent Application No. 094118087.
Intenational Search Report issued for corresponding International Patent Application No. PCT/US05/18465.
International Search Report and Written Opinion issued for corresponding International Patent Application No. PCT/US2006/034627.
International Search Report and Written Opinion issued for International Patent Application No. PCT/US05/18467 mailed Oct. 1, 2007.
International Search Report and Written Opinion issued for International Patent Application No. PCT/US05/18539 mailed Sep. 18, 2006.
International Search Report issued for International Patent Applicaiton No. PCT/US05/17839 mailed Aug. 10, 2006.
International Search Report issued for International Patent Application No. PCT/US05/18600 mailed Aug. 3, 2006.
International Search Report issued for International Patent Application No. PCT/US05/45316.
Supplementary European Search Report issued for corresponding European Patent Application No. EP 06802998.
U.S. Appl. No. 10/341,005, filed Jan. 13, 2003.
Dai, H. et al., "Controlled Chemical Routes to Nanotube Architectures, Physics, and Devices," J. Phys. Chem. B 1999, 103, 11246-11255.
Delzeit, L. et al., "Multilayered metal catalysts for controlling the density of single-walled carbon nanotube growth," Chemical Physics Letters 348 (2001) 368-374, Nov. 16, 2001.
Desai, A. et al., "Freestanding Carbon Nanotube Specimen Fabrication," Proceedings of 2005 5th IEEE Conference on Nanotechnology, Nagoya, Japan, Jul. 2005.
Dillon, A.C. et al., "A Simple and Complete Purification of Single-Walled Carbon Nanotube Materials," Adv. Mater. 1999, 11, No. 16, 1354-1358.
Franklin, N.R. et al., "An Enhanced CVD Approach to Extensive Nanotube Networks with Directionality," Adv. Mater. 2000, 12, No. 12.
Georgakilas, V. et al., "Organic Functionalization of Carbon Nanotubes," J. Am. Chem., Soc., vol. 124, No. 5, 2002, 760-761.
Gromov, A., "Purification of Carbon Nanotubes trends and methods," Caramel workshop Jan. 23, 2002, 1-13.
Haddon, R.C., et al., "Purification and Separation of Carbon Nanotubes," www.mrs.org/publications/bulletin, MRS Bulletin, Apr. 2004, 252-259.
Hafner, J.H. et al., "Catalytic growth of single-wall carbon nanotubes from metal particles," Chemical Physics Letters 296 (1998) 195-202, Oct. 30, 1998.
Hirsch, A., "Functionalization of Single-Walled Carbon Nanotubes," Angew. Chem. Int. Ed. 2002, 41, No. 11, 1853-1859.
Homma, Y. et al., "Single-Walled Carbon Nanotube Growth on Silicon Substrates Using Nanoparticle Catalysts," Jpn. J. Appl. Phys. vol. 41 (2002) Pt. 2, No. 1A/B.
Hou, P.X. et al., "Multi-step purification of carbon nanotubes," Carbon, 40 (2002) 81-85.
Huang, L. et al., "Time resolved spectroscopy of individual carbon nanotubes," Lasers and Electro-optics Society, 2004, LEOS 2004. The 17th Annual Meeting of the IEEE Rio Grande, Puerto Rico Nov. 8-9, 2004, Piscataway, NJ, USA, IEEE, vol. 1, Nov. 8, 2004, pp. 449-450.
Islam, M.F. et al., "High Weight Fraction Surfactant Solubilization of Single-Wall Carbon Nanotubes in Water," Nano Letters, 2003, vol. 3, No. 2, 269-273.
Jeong, T. et al., "A new purification method of single-wall carbon nanotubes using H2S and O2 mixture gas," Chemical Physics Letters 344 (2001) 18-22, Aug. 17, 2001.
Johnson, R.C., "IBM grows nanotube patters on silicon wafers," http://www.eetimes.com/articles/showArticle.jhtml?articleID=18307520, Sep. 30, 2002.

Joselevich, E. et al., "Vectorial Growth of Metallic and Semiconducting Single-Wall Carbon Nanotubes," Nano Letters xxxx, vol. 0, No. 0, A-E.
Kahn, M.G.C. et al., "Solubilization of Oxidized Single-Walled Carbon Nanotubes in Organic and Aqueous Solvents through Organic Derivatization," Nano Letters 2002, vol. 2, No. 11, 1215-1218.
Kong, J. et al. "Chemical vapor deposition of methane for single-walled carbon nanotubes," Chemical Physics Letters 292 (1998) 567-574.
Kong, J. et al., "Nanotube Molecular Wires as Chemical Sensors," Science, vol. 287, 622-625, Jan. 28, 2000, www.sciencemag.org.
Li, J. et al., "Carbon Nanotube Nanoelectrode Array for Ultrasensitive DNA Detection," Nano Lett., vol. 3, No. 5, 2003.
Li, Y. et al., "Growth of Single-Walled Carbob Nanotubes from discrete Catalytic Nanoparticles of Various Sizes," J. Phys. Chem. B 2001, 105, 11424-11431.
Li, Y. et al., "Preparation of monodispersed Fe-Mo Nanoparticles as the Catalyst for CVD Synthesis of Carbon Nanotubes," Chem. Mater. 2001, 13, 1008-1014.
Martinez, M.T. et al., "Modifications of single-wall carbon nanotubes upon oxidative purification treatments," Nanotechnology 14 (2003) 691-695.
Matarredona, O. et al., "Dispersion of Single-Walled Carbon Nanotubes in Aqueous Solutions of the Anionic Surfactant NaDDBS," J. Phys. Chem. B, 2003, 107, 13357-13367.
Mickelson, E.T. et al., "Solvation of Fluorinated Single-Wall Carbon Nanotubes in Alcohol Solvents," J. Phys. Chem. B. 103, 4318-4322.
Moore, V.C. et al., "Individually Suspended Single-Walled Carbon Nanotubes in Various Surfactants," Nano Letters, 20033, vol. 3, No. 10, 1379-1382.
Multi Disciplinair Project: Wonderous World of Carbon Nano Tubes, http://students.chem.tue.nl/ifp03/purification.html, Jun. 10, 2004.
Murphy, R. et al., "High-Yield, Nondestructive Purification and Quantification Method for Multiwalled Carbon Nanotubes," J. Phys. Chem. B 2002, 106, 3087-3091.
Nerushev, O.A. et al., "Carbon nanotube films obtained by thermal chemical vapour deposition," J. Mater. Chem., 11, 1122-1132.
Niu, C. et al., "High power electrochemical capacitors based on carbon nanotube electrodes," Appl. Phys. Lett. 70(11), Mar. 17, 1997.
Niyogi, S. et al., "Ultrasonic Dispersions of Single-Walled Carbon Nanotubes," J. Phys. Chem. B 2003, 107, 8799-8804.
O'Connell, M.J. et al., "Reversible water-solubilization of single-walled carbon nanotubes by polymer wrapping," Chemical Physics Letters 342 (2001) 265-271.
Onoa, G.B. et al., "Bulk production of singly dispersed carbon nanotubes with prescribed lengths," Nanotechnology 16 (2005) 2799-2803.
Parikh, K. et al., "Flexible vapour sensors using single walled carbon nanotubes," Sensors and Actuators B 113 (2006) 55-63.
Peigney, A. et al., "A Study of the Formation of Single- and Double-Walled Carbon Nanotubes by a CVD Method," J. Phys. Chem. B 2001, 105, 9699-9710.
Pompeo, F. et al., "Water Solubilization of Single-Walled Carbon Nanotubes by Functionalization with Glucosamine," Nano Letters, 2002, vol. 2, No. 4, 369-373.
Qi, P. et. al., "Toward Large Arrays of Multiplex Functionalized Carbon Nanotube Sensors for Highly Sensitive and Selective Molecular Detection," Nano Letters, 2003, vol. 3, No. 3, 347-351.
Research—Multifunctional Nanotube Composites, http://www.ornl.gov/~odg/compositesmain.html, Jun. 10, 2004.
Riggs, J.E. et al., "Optical Limiting Properties of Suspended and Solubilized Carbon Nanotubes," J. Phys. Chem. B, 2000, 104, 7071-7076.
Riggs, J.E. et al., "Strong Luminescence of Solubilized Carbon Nanotubes," J. Am. Chem. Soc. 2000, 122, 5879-5880.
Rinzler, A.G. et al., "Large-scale purification of single-wall carbon nanotubes: process, product, and characterization," Appl. Phys. A 67, 29-37 (1998).
Shelimov, K.B. et al., "Purification of single-wall carbon nanotubes by ultrasonically assisted filtration," Chemical Physics Letters 282 (1998) 429-434.
Sotiropoulou, S. et al., "Carbon nanotube array-based biosensor," Anal. Bioanal Chem. (2003) 375:103-105.

Star, A. et al., "Preparation and Properties of Polymer-Wrapped Single-Walled Carbon Nanotubes," Angew. Chem. Int. Ed. 2001, 40, No. 9, pp. 1721-1725.

Sun, X. et al., "Investigation of an optical limiting mechanism in multiwalled carbon nanotubes," Applied Optics, vol. 39, No. 12, Apr. 20, 2000.

Sun, Y. et al., "High Dissolution and Strong Light Emission of Carbon Nanotubes in Aromatic Amine Solvents," J. Am. Chem. Soc. 2001, 123, 5348-5349.

Sun, Y. et al., "Soluble Dendron-Functionalized Carbon Nanotubes: Preparation, Characterization, and Properties," Chem. Mater. 2001, 13, 2864-2869.

Valentini, L. et al., "Sensors for sub-ppm NO2 gas detection based on carbon nanotube thin films," Applied Physics Letters, vol. 82, No. 6, Feb. 10, 2003, 961-963.

Vivekchand, S. et al., "A new method of preparing single-walled carbon nanotubes," Proc. Indian Acad. Sci. (Chem Sci.) vol. 115, Nos. 5 & 6, Oct.-Dec. 2003, pp. 509-518.

Zhang, Y. et al., "Formation of metal nanowires on suspended single-walled carbon nanotubes," Applied Physics Letters, vol. 77, No. 19, Nov. 6, 2000.

Zhang, Y. et al., "Metal coating on suspended carbon nanotubes and its implication to metal-tube interaction," Chemical Physics Letters 331 (2000) 35-41, Nov. 24, 2000.

Zhang, Z. et al., "Select Pathways to Carbon Nanotube Film Growth," Adv. Mater. 2003, 13, No. 23, Dec. 3, 1767-1770.

Zhao, Y.-P. et al., "Frequency-dependent electrical transport in carbon nanotubes," Physical Review B, vol. 64, 201402(R), 1-4.

Brown, K. M., "System in package "The Rebirth of SIP"," 2004 IEEE Custom Integrated Circuits, May 2004, 6 pages.

Crowley, et al., "512 Mb PROM with 8 layers of antifuse/Diode cells," IEEE International Solid-State Circuits Conference, vol. XLVI, Feb. 2003, pp. 284-285.

Cui, et al., "Carbon Nanotube Memory Devices of High Charge," Applied Phys. Ltrs., vol. 81, No. 17, Oct. 2002, pp. 3260-3262.

Fuhrer, et al., "High-Mobility Nanotube Transistor Memory," Nano Letters, vol. 2, No. 7, 2002, pp. 755-759.

Jiang, et al., "Performance Breakthrough in 8nm Gate-All-Around Length Gate-All-Around Nanowire Transistors using Metallic Nanowire Contacts," 2008 Symposium on VLSI Technology Digest of Technical Papers, pp. 34-35.

Novak, et al., "Nerve Agent Using Networks of Single-Walled Carbon Nanotubes," Appl. Phys. Ltr., vol. 83, No. 19, Nov. 2003, pp. 4026-4028.

Star et al., "Nanoelectronic Carbon Dioxide Sensors," Adv. Mater., vol. 16, No. 22, 2004, pp. 2049-2052.

Star et al., "Nanotube Optoelectronic Memory Devices," Nano Letters, vol. 4, No. 9, 2004, pp. 1587-1591.

Zhou, et al., "p-Channel, n-Channel Thin Film Transistors and p—n Diodes Based on Single Wall Carbon Nanotube Networks," Nano Letters, vol. 4, No. 10, 2004, pp. 2031-2035.

Bahr, "Functionalization of Carbon Nanotubes by Electromechanical Reduction of Aryl Diazanium Salts: A Bucky Paper Electrodes," J. Am. Chem. Soc. vol. 123, No. 27, 2001, pp. 6536-6542.

Bahr, "Highly Funtionalized Nanotube Using in Situ Generated Diazanium Compounds," Chem. Mater., vol. 13, No. 11, 2001, pp. 3823-3824.

Banerjee, "Structural Characterization, Optical Properties & Improved Solubility of Carbon Nanotubes Functionalized with Wilkinson's Catalyst," J. Am. Chem. Soc., vol. 124, No. 30, 2002, pp. 8940-8948.

Banerjee, "Synthesis & Characterization of Carbon Nanotube—Nanocrystal Heterostructures," Nano Letters, vol. 2, No. 3, 2002, pp. 195-200.

Banerjee, "Location-Specific Biological Functionalization on Nanotubes: Attachment to Proteins at the Ends of Nanotubes using Nanocrystal Masks," Nano Letters, vol. 3, No. 3, 2003, pp. 283-287.

Beaucage, "The Functionalization of Oligonucleotides Via Phosphoramidite Derivatives," Tetrahedron, vol. 49, No. 10, 1993, pp. 1925-1963.

Chattopadhyay, "A Route for Bulk Separation of Semiconducting from Metallic Single-Wall Carbon Nanotubes," J. Chem. Soc., vol. 125, Feb. 22, 2003, pp. 3370-3375.

Dycke, "Solvent-Free Functionalization of Carbon Nanotubes," J. Am. Chem. Soc., vol. 125, No. 5, 2003, pp. 1156-1157.

Jenkins, "The Biosynthesis of Carbocyclic Nucleosides," Chem. Soc. Rev., 1995, pp. 169-176.

Lauret, "Third-Order Optical Nonlinearities of Carbon Nanotubes in the Femasecond Regime," App. Phys. Ltrs., vol. 85, No. 16, 2004, pp. 3572-3574.

Li, "High-Resolution Printing with Dendrimers," Nano Letters, vol. 2, No. 4, 2002, pp. 347-349.

Margulis, "Non-Degenerate Optical Four-Wave Mixing in Single-Walled Carbon Nanotubes," Optics Communications, vol. 249, 2005, pp. 339-349.

Rashid, "Self Assembled Organic Supramolecular Thin Films for Nonlinear Optics," Organic Electronics 5, 2004, pp. 147-155.

Star, "Electronic Detection of Specific Protein Binding Using NT FET Devices," Nano Letters, vol. 3, No. 4, 2003, pp. 459-463.

Williams, Carbon Nanotues with Dna Recognition, Nature, vol. 420, 2002, p. 761.

* cited by examiner

420

424

428

432

430

434

436
438
437

440

438

442

448

452

466

472

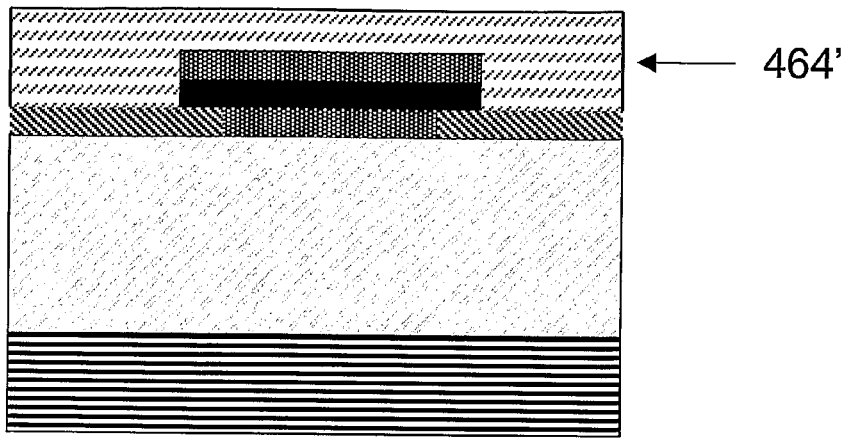
Figure 4L'  ← 464'
466'
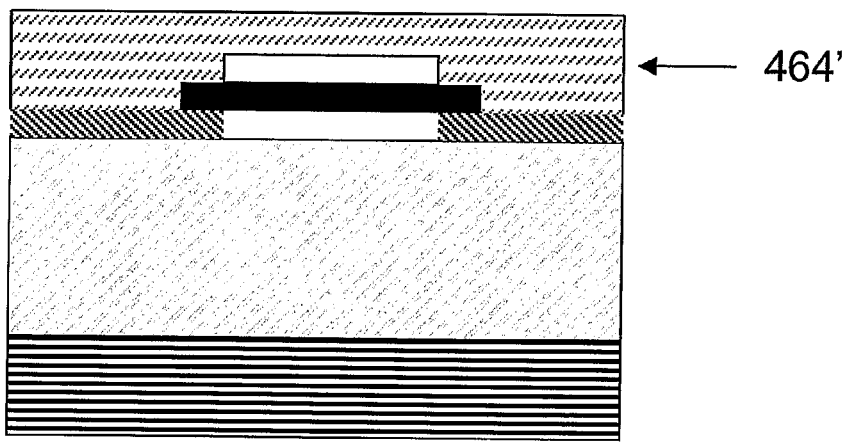
Figure 4M'  ← 464'
466'

NANOTUBE FABRIC-BASED SENSOR SYSTEMS AND METHODS OF MAKING SAME

CROSS-REFERENCE TO RELATED APPLICATIONS

This application is a U.S. National Phase Application under 35 U.S.C. §371 of International Patent Application No. PCT/US2006/034627, filed Sep. 6, 2006, entitled "Nanotube Fabric-Based Sensor Systems and Methods of Making Same," which claims the benefit under 35 U.S.C. §119(e) of U.S. Provisional Patent Application No. 60/714,388, filed Sep. 6, 2005 and entitled "Nanotube Fabric Sensor Platform," the entire contents of each are incorporated herein by reference.

This application is related to the following applications, the entire contents of which are incorporated herein by reference:

U.S. patent application Ser. No. 10/844,913, now U.S. Patent Publication No. 2005/0053525, filed May 12, 2004 and entitled "Sensor Platform using a Horizontally Oriented Nanotube Element;" and U.S. patent application Ser. No. 10/844,883, now U.S. Patent Publication No. 2005/0065741, filed May 12, 2004 and entitled "Sensor Platform using a Non-Horizontally Oriented Nanotube Element."

BACKGROUND

1. Technical Field

The present application relates generally to systems and methods for the detection of target analytes, the systems and methods including a nanotube aspect.

2. Discussion of Related Art

Chemical sensors and biosensors have been utilized for detecting many species, from contaminants in air (e.g., in air quality sensors) to the presence of particular DNA segments in blood samples or other samples. More recently, chemical and biosensors utilizing nanotubes, such as single-walled carbon nanotubes (SWNTs) have been proposed. See, e.g., J. Kong et al., *Science*, vol. 287, pp. 622-625 (Jan. 28, 2000), the entire contents of which are incorporated herein by reference.

Chemical sensors made of nanotubes may be functionalized or otherwise modified to become molecule-specific or species-specific sensors. Further details may be found in the following references, the entire contents of which are incorporated herein by reference: P. Qi et al., "Toward Large Arrays of Multiplex Functionalized Carbon Nanotube Sensors for Highly Sensitive and Selective Molecular Detection," *Nano Lett.*, vol. 3, no. 3, pp. 347-51 (2003); and Dai et al., "Carbon Nanotube Sensing," U.S. Patent Publication No. 2002/0179434, filed on Jun. 18, 2002. On the other hand, such sensors may comprise non-functionalized semiconducting tubes and may sense for the presence of known chemicals, see, e.g., Kong, supra.

Optical nonlinearity of thin films of nanotubes has been described, e.g., by Rashid, et al., "Self-Assembled Organic Supramolecular Thin Films for Nonlinear Optics", Organic Electronics 5 (2004) 147-155, the entire contents of which are incorporated herein by reference. Optical nonlinearity is a feature of some materials whereby the frequency of light reflected by a material is not equal to the frequency of the light that is transmitted onto that material. Lauret, J.-S., et al, "Third-order optical nonlinearities of carbon nanotubes in the femtosecond regime", Applied Physics Letters vol. 85, no. 16 (2004) 3572-2574 have described. Optical nonlinearities generally arise in nanotubes due to a change in polarization in the molecular structure of the nanotubes from an applied field. Because of the quantum confinement of the $\pi$-electrons associated with their 1-D structure, nanotubes have a large and fast electronic third-order non-linearity. For further details see Margulis, VI A., et al "Non-degenerate optical four-wave mixing in single-walled carbon nanotubes", Optics Communications, vol. 249 (2005) 339-349, the entire contents of which are incorporated herein by reference.

SUMMARY

The present invention provides nanotube fabric-based sensor systems and methods of malting same. The sensor platforms include nanofabric sensor elements, which in some cases include pristine nanotubes and in others include nanotubes functionalized with analyte-specific molecules. The platforms also include optical excitation and detection systems for measuring changes in the non-linear response of the nanofabric sensor element arising from an interaction between the element and one or more analytes, and from those changes determining the absence or presence of the one or more analytes.

Under one aspect, a system for sensing the presence of an analyte in a fluid includes a nanotube sensor element including a plurality of nanotubes and positioned for exposure to a fluid; an optical source capable of generating optical radiation, the radiation having a source frequency and a fluence selected to generate a nonlinear optical response by the nanotube sensor element; an optical detector capable of measuring the nonlinear optical response by the nanotube sensor element; and logic in electrical communication with the optical detector to sense the presence of an analyte in the fluid based on the nonlinear optical response measured by the optical detector.

One or more embodiments include one or more of the following features. The nanotube sensor element includes a nonwoven fabric of nanotubes. The nonlinear optical response of the nanotube sensor element includes the nanotube sensor element radiating optical energy at a different frequency than the source frequency. The nonlinear optical response of the nanotube sensor element includes radiation at the third harmonic of the source frequency. Attachment of the analyte to the nanotube sensor element changes the nonlinear optical response of the nanotube sensor element. Attachment of the analyte to the nanotube sensor element causes a charge transfer between the nanotube sensor element and the analyte. The charge transfer changes the nonlinear optical response of the nanotube sensor element. The logic is capable of determining the change in the nonlinear optical response of the nanotube sensor element caused by attachment of the analyte and thus sensing the presence of the analyte. The change in the nonlinear response of the nanotube sensor element includes a change in frequency of optical energy radiated by the nanotube sensor element. The optical detector detects the change in frequency of optical energy radiated by the nanotube sensor element. The nanotubes of the nanotube sensor element include pristine nanotubes. The nanotubes of the nanotube sensor element include nanotubes that are functionalized with analyte-specific molecules. The nanotubes of the nanotube sensor element include nanotubes that are derivitized with analyte-specific molecules. The nanotubes of the nanotube sensor element include nanotubes that are functionalized with a nonlinear material. The nonlinear material causes a change in the nonlinear optical response of the nanotube sensor element. The change in the nonlinear optical response includes a change in frequency of optical energy radiated by the nanotube sensor element. The nanotubes of the nanotube sensor element are functionalized so as to have or increase an affinity for a particular analyte. The nanotubes of the nanotube sensor element are derivitized so as to have or to increase an affinity for a particular analyte. The nanotube sensor element is functionalized so as to have or to increase an affinity for multiple analytes. The nanotube sensor element is derivitized so as to have or to increase an affinity for multiple analytes. The nanotube sensor element includes supports defining a gap over which at least a portion of the plurality of nanotubes is suspended. Further including material that clamps at least a portion of the plurality of nanotubes to at least a portion of the supports. The nanotube sensor element includes a substrate on which the plurality of nanotubes is disposed. The optical source includes a laser. The optical detector includes a photodiode. The nanotube sensor element further includes nanowires. The system is capable of sensing an analyte selected from the group consisting of a gaseous element, an airborne molecule, an organic molecule, an inorganic molecule, and a biological molecule. The biological molecule is selected from the group consisting of a peptide, a protein, and a nucleic acid. The nanotubes of the nanotube sensor element include substantially a monolayer of nanotubes.

Under another aspect, a method of using a nanofabric sensor to sense the presence of an analyte in a fluid includes characterizing a nanotube sensor element, the nanotube sensor element including a plurality of nanotubes, the characterization including irradiating the nanotube sensor element with a first optical beam having a frequency and a fluence selected to generate a first nonlinear optical response in the nanofabric sensor element, and measuring the first nonlinear optical response of the nanotube sensor element. The method also includes exposing the nanotube sensor element to a fluid; and characterizing the nanotube element after fluid exposure, the characterization including irradiating the nanotube sensor element with a second optical beam having a frequency and a fluence substantially the same as the frequency and fluence of the first optical beam to generate a second nonlinear optical response in the nanotube sensor element, and measuring the second nonlinear optical response of the nanotube sensor element. The method also includes comparing the first and second nonlinear optical responses of the nanotube sensor element to sense the presence of an analyte in the fluid.

One or more embodiments include one or more of the following features. The nanotube sensor element includes a non-woven fabric of nanotubes. The first nonlinear response of the nanotube sensor element is at a different frequency than the second nonlinear response of the nanotube sensor element. The frequency of the second nonlinear response of the nanotube sensor element is the third harmonic of the first nonlinear response of the nanotube sensor element. Further including functionalizing the nanotubes to have or to enhance an affinity for the analyte. Further including derivitizing the nanotubes to have or to enhance an affinity for the analyte. Further including functionalizing the nanotubes to have or to enhance an affinity for a plurality of analytes. Further including derivitizing the nanotubes to have or to enhance an affinity for a plurality of analytes. Generating the radiation with a laser. The fluid includes a gas. The fluid includes a liquid.

DETAILED DESCRIPTION

Preferred embodiments of the invention provide sensors and sensor arrays for biological and/or chemical sensing. They can be built using conventional semiconductor fabrication techniques and can leverage existing manufacturing infrastructure and processes to create sensors employing carbon nanotubes. The manufacturing techniques are largely compatible with CMOS processes and can be conducted at lower temperatures than those for making conventional nanotube-based structures. They allow fabrication of a massive number of sensors on a given chip or wafer that can be integrated with various forms of control and computational circuitry.

Most embodiments involve utilizing the non-linear optical effects of carbon nanotube (CNT) fabrics. Electromagnetic radiation interacts with and generates a non-linear optical response in the CNT fabric (or "nanofabric"). In many embodiments, the electromagnetic radiation that irradiates the nanofabric has a frequency $\omega_1$, and in response the nanofabric emits its own radiation with a frequency $\omega_2$. This process is analogous to harmonic generation, e.g., second harmonic generation, in which a laser beam at (or centered at) a frequency $\omega_1$ irradiates a material with specified non-linear attributes, which then emits its own light at a different frequency $\omega_2$, e.g., at the second harmonic of the laser beam frequency. In general, whenever electromagnetic radiation irradiates the nanofabric, the fabric produces radiation of a specific frequency. This radiation is detected by an optical detector, such as a photodiode.

During operation, a chemical or gas may interact with and bind to the nanofabric, which can alter the non-linear properties of the nanofabric. These altered properties may cause a change in the frequency of the emitted radiation, which will be detected by the detector; the change in frequency reflects the presence of chemicals and/or gases. For example, if the electromagnetic radiation is at frequency $\omega_1$, and the normal nanofabric nonlinear response is at frequency $\omega_2$, the binding of the gas or chemical to the nanofabric may shift the nanofabric's nonlinear response to a frequency $\omega_3$. This frequency change thus makes it possible to detect a wide range of chemicals and gases.

Figure 1A:
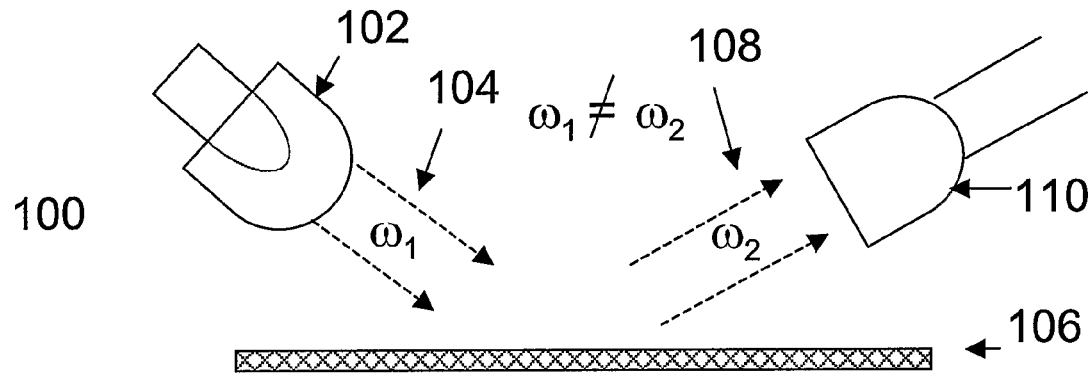
FIGS. 1A-C illustrate embodiments of nanosensor systems for detecting the presence of analytes at a nanofabric sensor element.
Figure 1B:
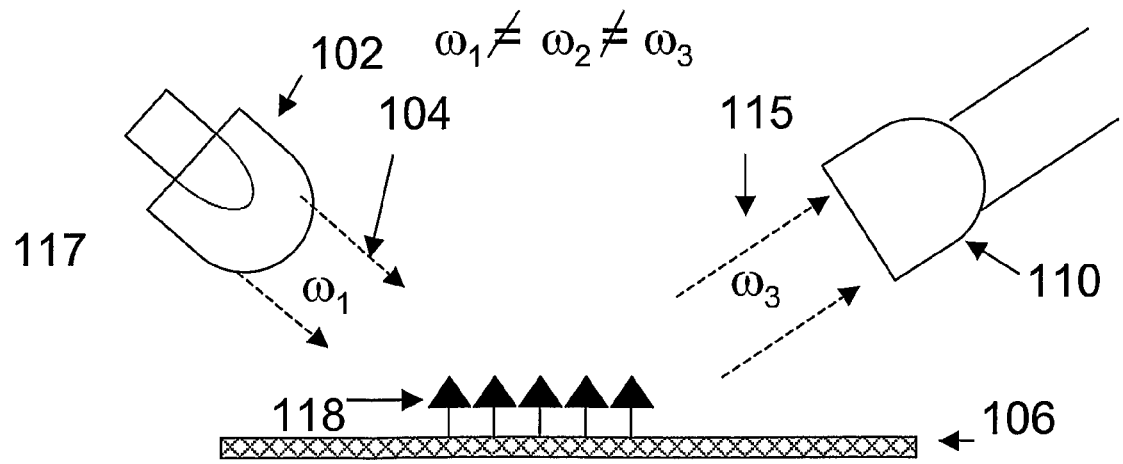

FIGS. 1A through 1B illustrate exemplary nanosensor systems. FIG. 1A shows a typical set-up to measure the non-linear response of a nanofabric element to irradiation. FIG. 1A illustrates nanosensor system 100 which includes a light source 102, e.g., a laser, generated light 104, e.g., a laser beam, nanofabric sensor element 106, modified light 108 and light detector 110, e.g., a photodiode. During operation, light source 102 emits generated light 104, which has a given frequency $\omega_1$. Generated light 104 may alternately have a bandwidth that is centered at frequency $\omega_1$ or otherwise can be characterized by frequency $\omega_1$. Generated light 104 irradiates and interacts nonlinearly with nanofabric sensor element 106, generating modified light 108 having frequency $\omega_2$. Frequency $\omega_2$ is a different frequency than the frequency of the generated light 104, i.e., $\omega_1 \neq \omega_2$. Note that the "conversion" of generated light 104 to modified light 108 is typically not perfectly efficient, e.g., not 100%, so some of the generated light 104 will also simply reflect from nanofabric sensor element 106, and will travel in generally the same direction as that of modified light 108. Detector 110 detects modified light at $\omega_2$, and may further include optics such as filters, e.g., bandpass or bandblock filters, or polarization optics, to substantially block residual generated light 104 and thus enhance the detector's sensitivity to light at $\omega_2$.

FIG. 1B illustrates a system similar to that shown in FIG. 1A, but in which a plurality of bound molecules 118 are attached to nanofabric sensor element 106. The bound molecules in this example are selected to bind pre-determined analyte molecules with a high degree of specificity. As discussed in further detail below, the plurality of bound molecules 118 may be covalently or otherwise bound to the nanotubes in nanofabric sensor element 106. The attachment of bound molecules 118 to nanofabric sensor element 106 modifies the nonlinear response of element 106 to generated light 104 at $\omega_1$, such that element 106 generates modified light 115 at frequency $\omega_3$, which is different both from $\omega_1$ and $\omega_2$.

Figure 1C:
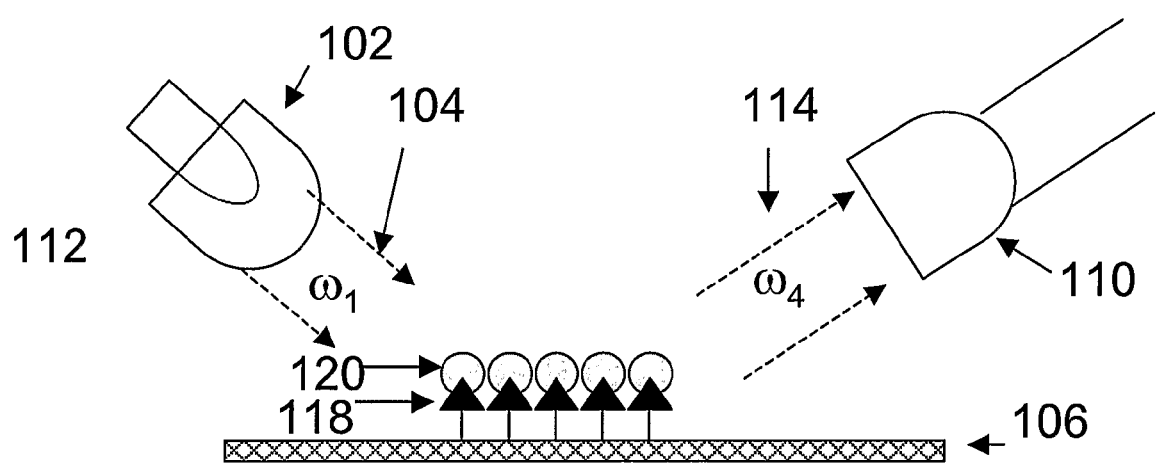

FIG. 1C illustrates the system of FIG. 1B, but further including a analyte species 120 attached to bound molecules 118. Here, the generated light 104 irradiates and interacts nonlinearly with nanofabric 106, to which is bound the complex of bound molecules 118 and attached analyte species 120. The attachment of complex 118, 120 to nanofabric sensor element 106 modifies the nonlinear response of nanofabric 106 to generated light 104 at $\omega_1$, such that nanofabric generates modified light 114 at frequency $\omega_3$, which is different frequency than $\omega_1$, $\omega_2$, and $\omega_3$. Detector 110 detects modified light 114 at least at $\omega_4$, and may include other optics such as filters or polarization optics to enhance its sensitivity to this frequency. Detector 110 may also detect light at $\omega_1$, $\omega_2$, and/or $\omega_3$. For example, modified light 115 at frequency $\omega_3$, which is generated by nanofabric sensor element 106 having attached bound molecules 118, could be used as a "control" condition which would then allow a later change to the modified light frequency, such as that caused by the attachment of analyte 120 to the bound molecules, to be measured and thus provide a positive result.

Various optical excitation can be used to irradiate the nanotube sensor element and thus generate a measurable nonlinear response. In many embodiments, light source 102 will include a laser that has a frequency $\omega_1$ and a fluence that is capable of sufficiently irradiating the nanotube sensor element so that the element generates a nonlinear response to the irradiation. In some embodiments, light source 102 will include a continuous wave (CW) laser. In other embodiments, light source 102 will include an ultrafast laser, e.g., a Ti:Sapphire or Nd:YAG laser, which operates at a given repetition rate. In general, the higher the laser fluence at the nanotube sensor element, the stronger the element's nonlinear response to the irradiation. An ultrafast laser will typically have a substantially higher fluence than a CW laser operating at the same average power and focused to the same spot size, and so may cause a nanofabric sensor element to have a stronger nonlinear response than it would with excitation by a CW laser.

Likewise, various optical detection systems can be used to determine the change in the nanotube sensor element's non-linear optical response to optical excitation. The optical detection system may be selected to appropriately measure the nonlinear response that the light source causes the nanofabric sensor element to generate. Logic in electrical contact with the optical detector then measures the presence of one or more analytes based on the nonlinear optical response measured by the optical detection system.

Although the band gap of CNTs makes them highly responsive to infrared radiation in many embodiments, a wide range of radiation wavelengths, e.g., from UV to IR wavelengths, can be used in other embodiments, depending on the desired output signal.

Non-linear nanosensors can be readily fabricated by using standard CMOS and SOI integration techniques. As for other kinds of nanofabric sensors, such as those having an electrical characterization as described in U.S. Patent Publication Nos. 2005/0053525 and 2005/0065741, large arrays of sensors can be constructed to detect a large amount of species with a low false positive or false negative detection.

As will be described in more detail below, preferred embodiments elements made from a fabric of nanotubes ("nanofabrics"). Further details of nanofabrics, nanofabric elements, and methods of making same, may be found in the incorporated patent references, given below. The nanofabric elements may be unmodified (i.e., "pristine"), derivitized, or functionalized, so that they may be used to detect chemical analytes, such as gaseous elements, airborne molecules, organic and inorganic molecules. In certain embodiments, the chemical analyte may be a biological molecule such as peptides, proteins, or nucleic acids. For example, the nanofabric may be functionalized, either non-covalently or covalently (e.g., by derivatization) so as to interact specifically with a particular analyte. The modified or unmodified analyte-sensitive nanofabrics may be incorporated into a nanosensor system for detection of the corresponding analyte in a sample. Without wishing to be bound by theory, it is believed that charge transfer between the (optionally functionalized) nanofabric and attached, e.g., adsorbed, analyte molecules changes the nonlinear response of the nanofabric to generated light. This in turn modifies the frequency of light that the nanofabric generates in response to the generated light, relative to the frequency of light that would be generated by the nanofabric alone, or the functionalized nanofabric alone. Preferred embodiments provide methods and compositions for the detection of target analytes using changes in the frequency of light that the nanofabric generates in response to irradiation, upon binding of the analytes.

Other embodiments utilize nonlinear properties of nanoparticles that are adhered to the sidewall of the CNTs to produce the desired change in frequency (optical output properties) of emitted radiation. Nanoparticles that are more susceptible to second order, fourth-order, etc nonlinearities can be adhered to the CNTs to generate a larger range of frequency changes. The CNT fabric has the added role of providing a supporting matrix to the nanoparticles which may exhibit nonlinear behavior. The inclusion of the nonlinear nanoparticles will increase the range and sensitivity of the chemical/gaseous detection.

Figure 2A:
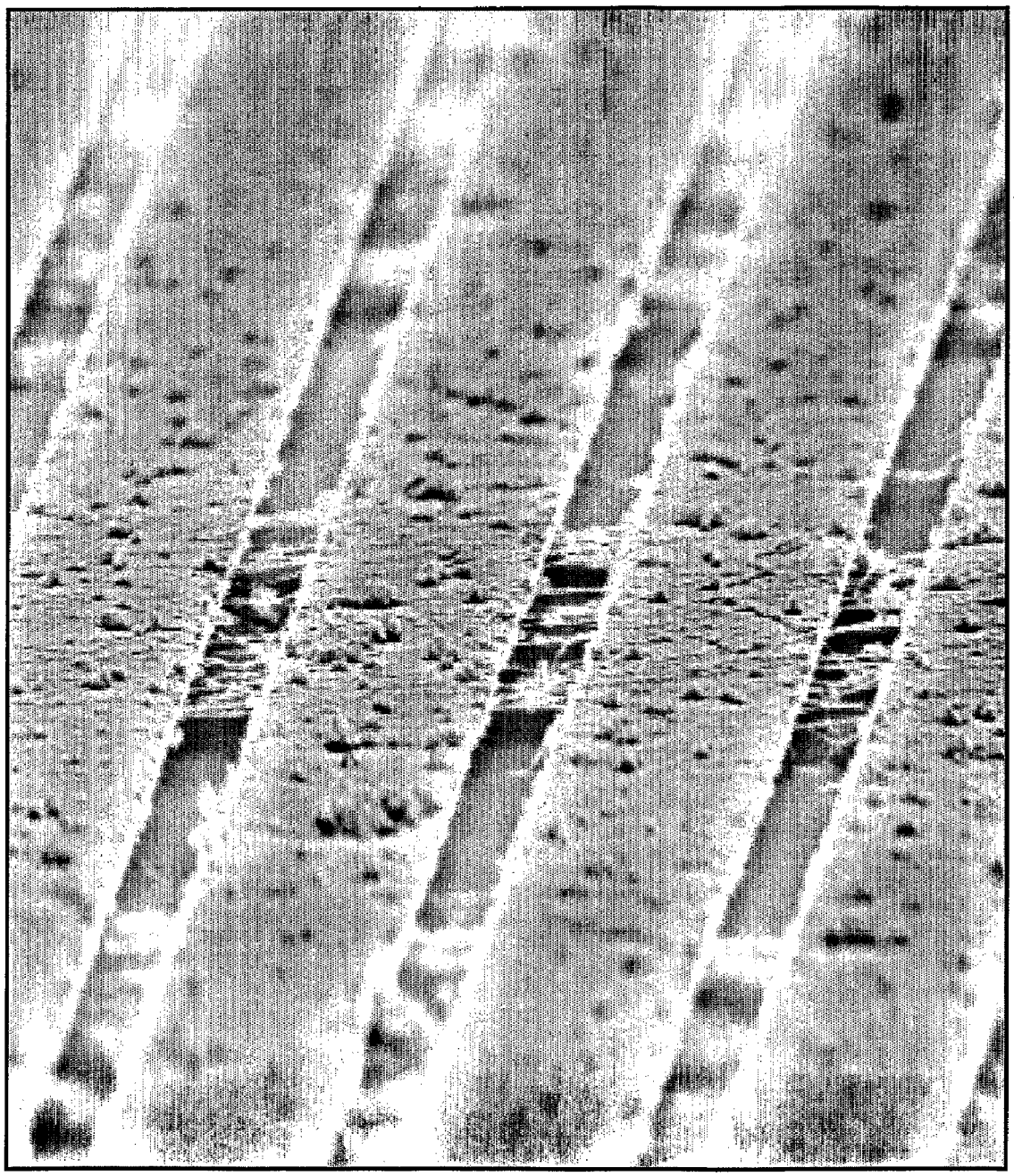
FIGS. 2A and B are micrographs of exemplary nanotube fabrics.
Figure 2B:
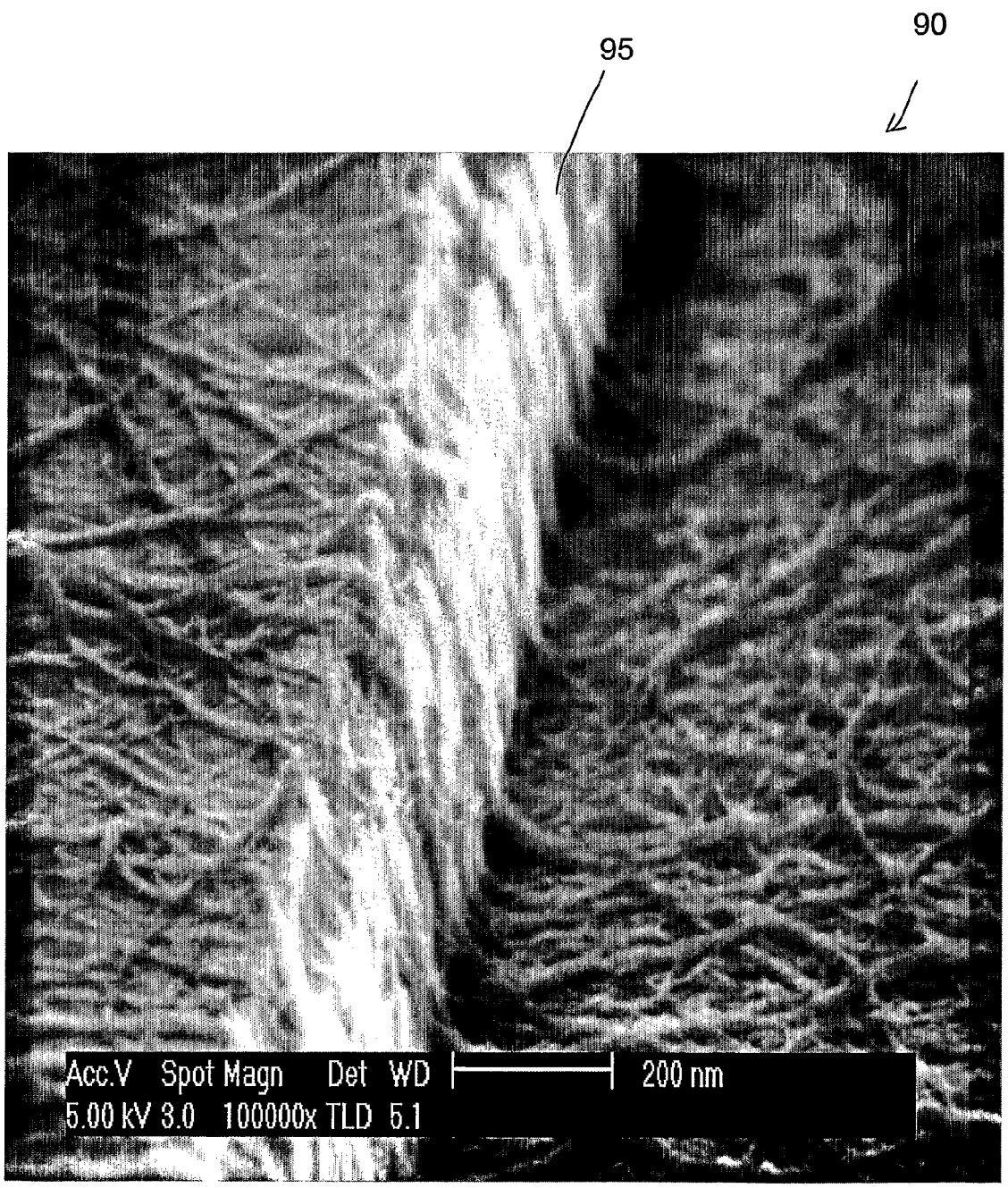

FIGS. 2A and B are micrographs of actual nanofabrics. FIG. 2A shows a nanofabric that is suspended over gaps defined by features in the underlying substrate. FIG. 2B shows a nanofabric that conforms to three-dimensional features of the underlying substrate. The fabric thickness, nanotube density, suspension, and conformal character can be controlled by altering application parameters, e.g., as more fully described in the incorporated patent references.

Many nanosensor embodiments are compatible with protocols that substantially prevent non-specific binding of non-target analytes. For an example of non-specific binding prevention, see Star et al., "Electronic Detection of Specific Protein Binding Using Nanotube FET Devices," *Nano Lett.*, vol. 3, no. 4, pp. 459-63 (2003), the entire contents of which are incorporated herein by reference.

The nanofabric of certain embodiments is formed from a non-woven fabric or layer of matted nanotubes (described in more detail below and also described in the incorporated patent references). Under certain embodiments, the fabric is formed of single-walled carbon nanotubes (SWNTs), but other embodiments may utilize multi-walled carbon nanotubes (MWNTs) or mixtures of single- and multi-walled carbon nanotubes or other nanoscopic elements, such as nanowires. The fabric of certain embodiments has nanotubes with substantially constant porosity. This porosity may be substantially determined by, for example, the number and density of spin coats, which commonly also plays a principal role in substantially determining the capacitance of a particular nanofabric.

Upon successful completion of the sensing activity, it may be desirable to be able to reset a device in the field. In order to accomplish such a reset, it is possible that an electrical pulse able to cause removal of a sensed molecule from a nanofabric sensor element could be provided to clear or zero the state of the element. Necessary voltages could be determined for individual element types specifically or could be part of an overall reset pattern which might simultaneously clear all of the elements from their states at a particular time. Such a reset feature would allow elements to become saturated with analytes but then to be returned to their original state so that the device could be reused. Reusability would reduce overall cost and maintenance requirements. For further details on reusing nanofabric-based sensors, see U.S. patent application Ser. No. 10/844,913, entitled "Sensor Platform Using a Horizontally Oriented Nanotube Element", filed May 12, 2004.

Exemplary Architectural Sensor Platforms

Figure 3A:
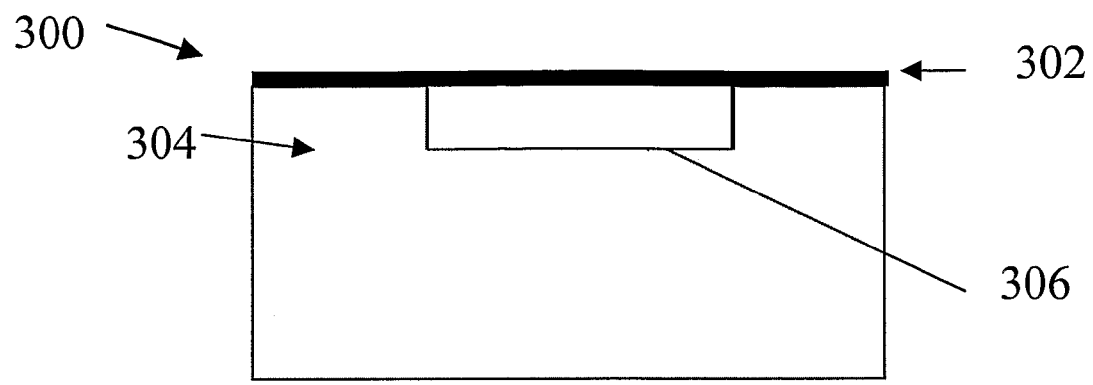
FIGS. 3A-C illustrate embodiments of nanofabric sensor elements.
Figure 3B:
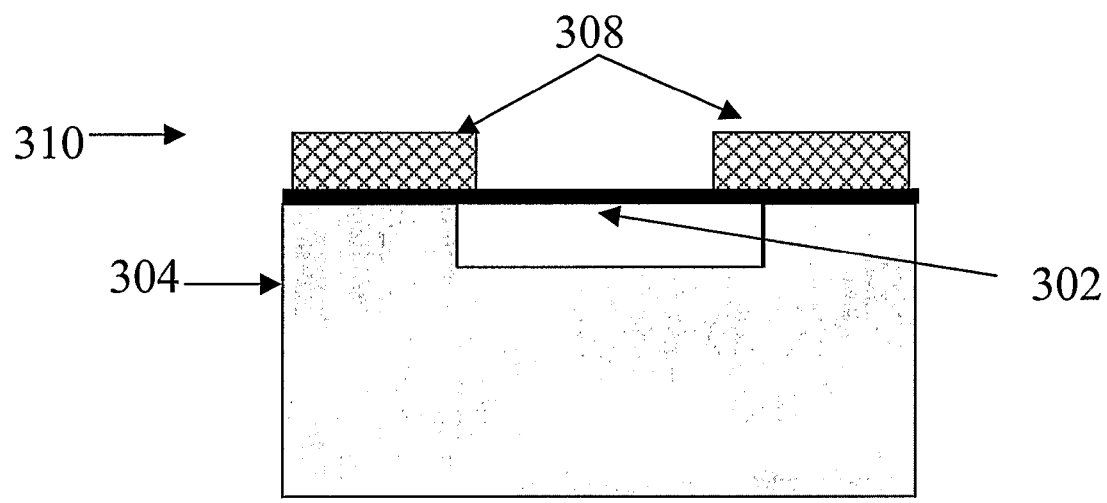
Figure 3C:
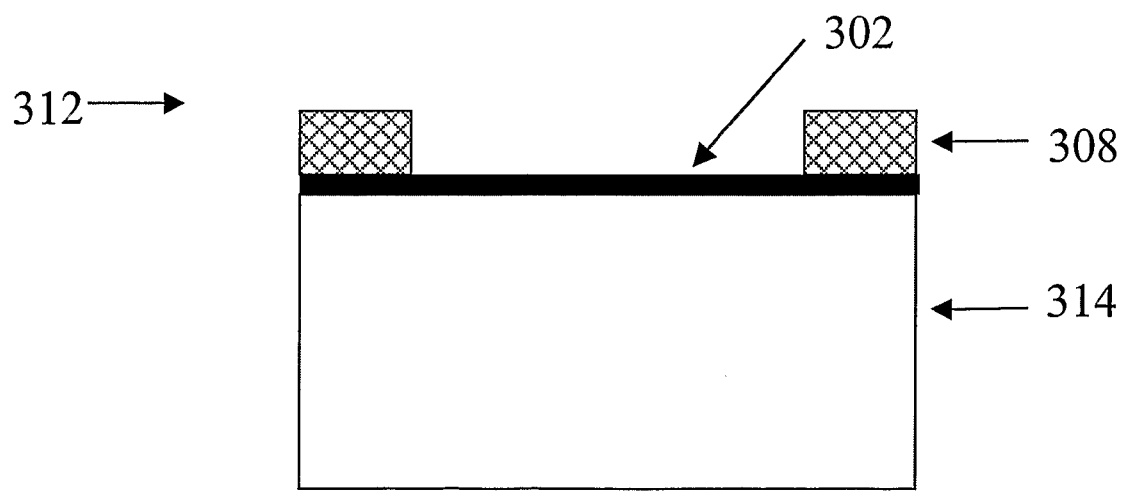

FIGS. 3 A-C illustrate various exemplary architectures of nanofabric sensor elements that can be used in the system of FIGS. 1A-1C. As will be described in greater detail below, the nanofabric in the element may be derivatized or functionalized after fabrication of the platform; in some embodiments, the derivatization or functionalization of the nanofabric may be incorporated into intermediate manufacturing steps of forming the nanofabric sensor element. In FIGS. 3A-3C, an individual nanofabric sensor element is shown, but, as will be clear from the description below, the utilization of well-known semiconductor manufacturing techniques allows these individual nanofabric sensor elements to be fabricated on a massive scale so that a given chip or wafer may have a very large number of elements that may be essentially identical to one another. The cells may be organized into massive arrays, small groups, or individual entities. This part of the description focuses on the architecture and basic platform. Subsequent sections discuss how the properties of the nanofabric itself may be tailored in specific ways to achieve specific desired effects.

FIG. 3A illustrates structure 300, which includes nanofabric layer 302, supports 304, and gap 306. Manufacture of such a structure is described below in reference to FIG. 4 et seq., as well as in the incorporated patent references. In this embodiment, the nanofabric is suspended over a gap 306 defined by supports 304.

FIG. 3B illustrates structure 310, which has a suspended nanofabric sensor 302, supports 304, gap 306 and pinning elements 308. Pinning elements 308 firmly attach or clamp the nanofabric element 302 to the supports and may be made from many different types of materials. Such materials are chosen from those compatible with the manufacture of the structure and with the particular sensing application desired. Exemplary materials may be found in the incorporated patent references.

FIG. 3C illustrates nanofabric sensor element 312. In this embodiment, nanofabric element 316 is disposed on support material 314, along with optional pinning structures 308. Support material 314, which may also be characterized as a pinning structure, may be anything consistent with use as a sensor, including but not limited to metals, alloys, ceramics, semiconductors, plastics, glass, etc. Such a pinning structure can allow facile electrical connection to the nanofabric as well as providing support or clamping of the nanofabric to the underlying structure 314. A pinning structure would in many cases be conductive, but can be insulating or conductive, depending on the application.

Techniques for Tailoring Characteristics of Nanofabric Elements

Many specific methods of preparing the nanofabric can be envisioned, depending upon the specific sensing requirements for a particular device. Tuning methods of production, and the resulting products, to device requirements can be performed by using a combination of spin coating and photolithography in conjunction with functionalization or derivatization as described herein.

Nanofabrics may be created by chemical vapor deposition (CVD) or by applying prefabricated nanotubes onto a substrate (e.g., spin coating). Various exemplary techniques are described in the incorporated and/or published patents and patent applications identified above.

In the event that CVD-grown nanotubes are to be utilized, derivatization or functionalization of the fabric is straightforward. A CVD-grown nanofabric can be derivatized or functionalized in the same fashion as the spin-coated fabric. Nanotubes grown by CVD can be doped during the growth process with a limited number of materials such as boron, silicon, indium, germanium, phosphorous, arsenic, oxygen, selenium, and other monatomic species using current technologies. After the CVD process has been completed, CVD-grown nanotubes can be easily doped with an even wider variety of materials, including many types of molecules—for example, chemicals, drugs, DNA, RNA, peptides, or proteins.

The fabrication of nanofabrics by spin coating or otherwise depositing pre-formed nanotubes is described in the incorporated patent references. Such an approach has advantages over fabrication of nanofabrics by CVD. For example, lower temperatures may be used for manufacture of the device. This allows more materials to be used as a potential substrate in conjunction with the nanofabric element. In addition, prefabricated nanotubes may be derivatized or functionalized with nearly limitless agents before the nanotubes are applied to a substrate.

Other techniques for forming the nanofabric may be used as well—e.g., aerosol application, dipping, or any other appropriate method.

Nanofabric sensors may include semiconducting nanotubes, metallic nanotubes or both. Investigators have shown that metallic nanotubes may be separated from semiconducting nanotubes by precipitation. See, e.g., D. Chattopadhyay et al., "A Route for Bulk Separation of Semiconducting from Metallic Single-Walled Carbon Nanotubes," *J. Amer. Chem. Soc.*, vol. 125, pp. 3370-75 (Feb. 22, 2003), the entire contents of which are incorporated herein by reference. It is therefore an aspect of certain embodiments of the present invention to create nanofabrics of controlled composition (semiconducting vs. metallic) using this or any other method of separation. According to one precipitation method, single-walled nanotubes are acid-treated and then functionalized non-covalently—e.g., in octadecylamine and tetrahydrofuran—causing metallic species to precipitate out of solution while leaving semiconducting nanotubes in solution. Either of the separate lots of nanotubes may be used for nanofabric creation once they are separated from one another. Separated nanotubes may be used to create nanofabrics for use as nanosensors with or without functionalization, and such nanotubes may be used in spin-coating applications and other appropriate methods as explained herein and in incorporated references. Furthermore, the relative concentrations of semiconducting and metallic nanotubes may be controlled. For example, one may create a fabric of approximately 90% semiconducting tubes and 10% metallic nanotubes by mixing a solution of 100% semiconducting nanotubes with a solution of unseparated nanotubes to acquire the desired concentration of each type of nanotube. Solutions of 100% semiconducting tubes may be mixed with solutions of 100% metallic nanotubes as well.

Once formed, the nanofabric can be patterned by using standard lithography techniques, as described in the incorporated and published patent references. Such lithography techniques allow patterning of nanofabric by permitting the controlled definition of a region of fabric for use as a sensor element—for example, in the form of a nanotube ribbon of substantially predetermined dimensions.

Exemplary Types of Nanofabric Sensor Elements

A nanofabric sensor element can include carbon nanotubes or other highly robust materials, including nanowires that can operate under extreme conditions with no loss of sensitivity. Four general types of nanofabric sensor elements have been envisioned, which include:

pristine nanotubes (i.e., non-functionalized nanotubes)
non-covalently functionalized nanotubes
covalently derivatized nanotubes
a hybrid mixture of above.

1. Non-Functionalized, or Pristine, Nanotubes

A first type of nanofabric sensor element utilizes pristine nanotubes in the nanofabric element—that is, the nanotubes are non-functionalized nanotubes. The surfaces of the nanotubes will adsorb analytes, which will alter the nonlinear optical properties of the resulting complex as compared to the pristine nanotubes alone.

Under this approach, nanotubes may adsorb molecules or species onto their surfaces, resulting in a measurable change in frequency of the generated light.

2.-4. Functionalized Nanotubes

Functionalizing of nanotubes may be employed to enhance the fabric's ability to sense chemical and biological species. The functionalizing agent may be molecule specific, allowing for the attachment of specific species onto the nanotubes, or the functionalizing material may also be a nonlinear material which produces its own unique output frequency.

Before nanotubes are applied to a surface to create a nanofabric, they can be functionalized in solution in order to increase the bonding of the tubes to a surface and/or to make possible the bonding of, or interaction with, analytes. Such functionalized nanotubes can be used to create nanofabric sensor elements, especially by patterning the nanofabric into specific shapes.

Nanotubes may be functionalized in suspension before they are used to create a nanofabric, and such functionalized tubes may be stored in bulk before use. Such bulk-functionalized nanotubes may be mixed with pristine nanotubes to generate a partially functionalized nanofabric. More than one variety of functionalized nanotube solutions may be combined to generate mixtures of nanotubes to make mixed-functionalized nanofabrics. This procedure can be repeated to generate nanofabrics having as many different species of functionalized nanotubes as is desired for sensing. Thus, one could, for example, functionalize a nanotube solution with DNA sequences or RNA sequences to sense from a test sample just particular species of interest, such as those associated only with a specific virus or with proteins associated solely with specific forms of cancer. Some embodiments detect specific antigens or major histocompatibility complex (MHC)/antigen complexes from mixtures of fluids to be tested as an early warning sensor of disease or infection.

In other embodiments, nanotubes may be functionalized after nanotubes have been applied to a substrate in order to create a nanofabric. In this case, solution or gas phase functionalization could proceed before or after patterning the nanofabrics. This technique would lend itself to multiple spatially-addressable functionalization events across a surface. For example, one could envision using an inkjet-like process to spray various types of functionalizing agents onto specific regions of a substrate. Subsequent steps could be used to apply additional functional groups in the same or different regions to make nanofabric sensor elements with regionally tailored sensing agents on the same substrate. In this way, many different types of analytes could be sensed by a given array, potentially with each cell sensing for the presence of a different analyte, when light is systematically transmitted onto the various sectors of the array and the light generated by the nonlinear interaction between each cell and the transmitted light is detected, and the generated frequency is interpreted.

In yet other embodiments, nanotubes may be functionalized after sensing regions are patterned out of the bulk nanofabric. The incorporated patent references include exemplary details on creating and patterning nanofabrics. Upon completion of patterning, individual regions can be functionalized to serve as specific sensors. Multiple serial functionalizations or mixtures of functionalizing agents can be used to generate hybrid sensors capable of sensing more than one analyte at a time on a patterned nanofabric section or many such sections. This property lends itself to automation and use with robotics.

Suitable analytes include organic and inorganic molecules, including biomolecules. In a preferred embodiment, the target analyte may be an environmental pollutant(s), including pesticides, insecticides, toxins, etc.;
a chemical or chemicals, including solvents, polymers, organic materials, etc.;
one or more types of therapeutic molecules, including therapeutic and abused drugs, antibiotics, etc.;
one or more types of biomolecules, including hormones, cytokines, proteins, lipids, carbohydrates, cellular membrane antigens and receptors (neural, hormonal, nutrient, and cell surface receptors) or their ligands, etc;
whole cells, including prokaryotic (such as pathogenic bacteria) and eukaryotic cells, including mammalian tumor cells;
viruses, including retroviruses, herpes viruses, adenoviruses, lentiviruses, etc.; and
spores; etc.

For example, potential analyte molecules include nucleic acids, oligonucleotides, nucleosides, and their grammatical equivalents, as well as any and all modifications and analogs thereof, as understood in the art—including, for example, amino- or thio-modified nucleosides, and nucleotide molecules with alternate backbones or containing one or more carboxylic sugars, for example as described in the following references, the entire contents of which are incorporated herein by reference: Beaucage et al., *Tetrahedron*, vol. 49, no. 10, p. 1925 (1993); and Jenkins et al., *Chem. Soc. Rev.*, pp. 169-176 (1995). Hence, quite generally, molecules having at least two nucleotides covalently linked together could be potential analytes. Further, the category of potential analytes encompasses both single-stranded and double-stranded nucleic acids, as well as nucleic acids containing portions of both double-stranded and single-stranded sequences. Similarly, a potential nucleic-acid analyte could be DNA (including genomic or cDNA), RNA, or a hybrid, where the nucleic acid contains any combination of deoxyribo- and ribo-nucleotides, and any combination of bases, including uracil, adenine, thymine, cytosine, guanine, inosine, xathanine, hypoxathanine, etc. Mimetic compounds for any of the above might also act as potential analytes. In like fashion, potential analytes include proteins, oligopeptides, peptides, and their analogs, including proteins containing non-naturally occurring amino acids and amino-acid analogs, and peptidomimetic structures.

One skilled in the art will understand that a large number of analytes may be detected using various embodiments. Any target analyte for which a binding ligand, described herein, may be made may be detected using the methods and articles of various embodiments.

Nanoimprint lithography may be used as a method of applying functionalization agents to discrete portions of nanofabric and thus to create discrete nanosensors. Such a method is primarily used for making massive arrays with sub-100 nm features. Inkjet printing technology may be used for applying functionalization agents to discrete portions of a nanofabric to create separate nanosensors on a given wafer. Inkjet printing can be used to automate the functionalization of discrete nanofabric sensor elements, either by applying functionalization agent to nanofabric sensor elements directly, or by applying functionalized nanotubes to the area where a nanofabric sensor element would reside on a substrate. Inkjet printing is a non-impact, dot-matrix printing technology in which droplets of ink or, in this case, nanotube solutions are "jetted" from a small aperture directly to a specified position on a surface or medium to create an image. The light transmitter can then be directed at each of the sensing regions systematically, i.e. the entire array can be manipulated such that each region falls under a light source and nonlinearly generated light can be detected and analyzed, then the array (or the light source and detector) can be moved so that a different sensor can be analyzed.

Investigators have described a way of immobilizing proteins at specific locations on nanotubes. See I. Baneijee et al., "Location-Specific Biological Functionalization on Nanotubes: Attachment to Proteins at the Ends of Nanotubes Using Au Nanocrystal Masks," *Nano Lett.*, vol. 3, no. 3, pp. 283-287 (2003), the entire contents of which are incorporated herein by reference. Nanosensors can be made using proteins immobilized at the ends of nanotubes to sense for complementary species. According to this method, nanocrystals of gold are applied to the sidewalls of nanotubes, and avidin is adsorbed onto the entire surfaces of the nanotubes. A chemical etch procedure is performed to remove the gold nanocrystals and therefore also remove the avidin overlying the gold nanocrystals, leaving only the avidin attached to the ends of the nanotubes. Thus certain embodiments fabricate nanosensors using this procedure and immobilize protein and any other appropriate molecule at the ends of nanotubes used in nanosensing cells, articles, and elements, such that the bound molecule can be used in a ligand-specific regime.

The resulting nanofabric sensor elements are generally exposed to analytes, either as a part of a fully or nearly fully exposed system or as part of an encapsulated system whereby analytes are introduced in a controlled way. For example, the nanofabric sensor element of a gas sensor may be fully exposed to the air, whereas the nanofabric sensor element of a DNA sensor might be encapsulated within a complex microfluidic analyte introduction mechanism. With regard to the latter, see PCT publication WO 00/62931, "The Use of Microfluidic systems in the Electrochemical Detection of Target Analytes," the entire contents of which are incorporated herein by reference. A fluid containing analytes may be introduced to a sensing chamber by way of microchannels. Optional storage chambers and cell lysing chambers may be connected to the system by way of other microchannels. Certain embodiments thus utilize nanofabric sensor elements along with light transmission and detection schemes with such microfluidic systems.

Nanofabric sensor elements according to certain embodiments may also be used as a detector according to the principles disclosed in U.S. Pat. No. 6,361,958 to Sheih, the entire contents of which are incorporated herein by reference. A microfluidic device may include microchannels that have separated regions that have a member of a specific binding pair member such as DNA or RNA bound to porous polymer beads or structures fabricated into the microchannel. The microchannels may be fabricated from plastic and are operatively associated with a fluid-propelling component and detector. Thus a nanofabric sensor element and light transmission and detection platforms into the system of the '958 patent to Sheih.

The nanosensors according may also be used for analyte delivery and detection in conjunction with the nanofluidic channels described in incorporated references.

2. Non-Covalent Functionalization

A second type of nanofabric sensor element utilizes a nanofabric element in which nanotube surfaces are non-covalently functionalized. This allows for interaction with a wide variety of cations, anions, metal ions, small molecules, DNA, and proteins.

Non-covalent functionalization takes advantage of non-covalent bonding of molecules to the sidewalls of nanotubes with substantial retention of the chemical structure of the nanotubes. Nanofabric sensor elements can take advantage of such functionalization of nanotubes to increase, or make possible, bonding of nanotubes to analyte molecules or atoms. Nanofabrics may be non-covalently functionalized by adding pyrenes or other chemicals that are known to bind to nanotubes or graphite. For example, 1-pyrenebutanoic acid and succinimidyl ester in organic solvent, such as dimethylformamide or methanol, can be used to generate a succinimydyl functionalized nanotube. This method takes advantage of the pyrenyl group's interaction with the sidewalls of the nanotubes while generating succinyl ester groups that are highly reactive with nucleophilic substitution by primary and secondary amines found on the surfaces of most proteins and peptides as well as many drug and pro-drug compounds—where a "pro-drug" is, for example, an inactive precursor of a drug that is converted into active form in the body by normal metabolic processes. This functionalization mechanism is used to immobilize proteins and a wide variety of other biomolecules onto the sidewalls of SWNTs and to sense specifically for molecules that conjugate or bind those immobilized molecules preferentially. For example, streptavidin may be adsorbed onto a nanotube surface in order to be used in immunohistochemical sensing. See Chen et al., "Non-covalent Sidewall Functionalization of Single walled Carbon Nanotubes for Protein Immobilization," *J. Am. Chem. Soc.*, vol. 123, pp. 3838-39 (2001), the entire contents of which are incorporated herein by reference. The use of such nanosensors is compatible with analyte detection systems where non-specific binding is prevented. See, e.g., Star et al., "Electronic Detection of Specific Protein Binding Using Nanotube FET Devices", *Nano Lett.*, vol. 3, no. 4, pp. 459-63 (2003), the entire contents of which are incorporated herein by reference.

Many methods are known for non-covalently functionalizing nanotubes. See, e.g., the following references, the entire contents of which are incorporated herein by reference: J. Kong et al., "Nanotube Molecular Wires as Chemical Sensors," Science, vol. 287, pp. 622-25 (Jan. 28, 2000); U.S. Pat. No. 6,528,020; and U.S. Pat. Appl. No. 2002/0172963 to Kelley et al., "DNA-Bridged Carbon Nanotube Arrays." For example, coating of a nanotube with PMMA (polymethylmethacrylate) has been shown to sensitize the nanotube to $NO_2$ gas, and gold decoration of a nanotube has been shown to sensitize it to the presence of a thiol vapor, see U.S. Pat. No. 6,528,020, the entire contents of which are incorporated herein by reference. In fact, since nanotubes retain similar properties to graphitic sheets, nearly any method suitable for non-covalently functionalizing graphite may be used to functionalize nanotubes.

3. Covalent Functionalization

The third type of sensor utilizes a nanofabric element in which a covalently derivatized nanotube surface allows any of the interactions above.

Nanotubes have been functionalized using covalent chemical bonding Methods—e.g., involving diazonium salts. Further details may be found in the following references, the entire contents of which are incorporated herein by reference: J. L. Bahr et al., "Functionalization of Carbon Nanotubes by Electrochemical Reduction of Aryl Diazonium Salts: A Bucky Paper Electrode," *J. Am. Chem. Soc.*, vol. 123, no. 27, pp. 6536-42 (2001); J. L. Bahr et al., "Highly Functionalized Carbon Nanotubes Using in Situ Generated Diazonium Compounds," *Chem. Mater.*, vol. 13, no. 11, pp. 3823-24 (2001). Other workers have used solvent-free methods such as aniline in isoamyl nitrate. See, e.g., C. A. Dyke et al., "Solvent-Free Functionalization of Carbon Nanotubes," *J. Am. Chem. Soc.*, vol. 125, no. 5, pp. 1156-57 (2003), the entire contents of which are incorporated herein by reference. Still others have used oxidative processes to functionalize nanotubes in one-pot reactions, in which reactions occur in a single reaction vessel. See, e.g., M. G. C. Kahn et al., "Solubilization of Oxidized Single-Walled Carbon Nanotubes in Organic and Aqueous Solvents through Organic Derivatization," *Nano Lett.*, vol. 2, no. 11, pp. 1215-18 (2002), the entire contents of which are incorporated herein by reference. Yet others have covalently bound peptide nucleic acid sequences to single-walled carbon nanotubes. See, e.g., K. A. Williams et al., "Carbon nanotubes with DNA Recognition," *Nature*, vol. 420, p. 761 (2002), the entire contents of which are incorporated herein by reference.

For example, Williams et al., supra, uses an approach to providing covalently functionalized nanotubes in which the unique properties of a nanotubes are combined with the specific molecular-recognition features of DNA by coupling a nanotube to peptide nucleic acid (PNA, an uncharged DNA analog) and hybridizing these macromolecular wires with complementary DNA. Following this example the inventors envision that such hybridization will be appropriate for nanofabrics as well. This allows the incorporation of DNA-derivatized nanofabrics into larger electronic devices by recognition-based assembly, and allows using nanofabrics as probes in biological systems by sequence-specific attachment. The technique used to couple nanofabrics covalently to PNA involves ultrasonically shortening nanofabric ropes for 1 hour in a 3:1 mixture of concentrated $H_2SO_4$ and $HNO_3$. Subsequent exposure to 1 M HCl produces abundant carboxyl end-groups. This material is then dispersed in dimethylformamide (DMF, 99.5%) and incubated for 30 min in 2 mM 1-ethyl-3-(3-dimethylaminopropyl)carbodiimide hydrochloride and 5 mM N-hydroxysuccinimide (NHS) to form nanofabric-bearing NHS esters. PNA adducts are then formed by reacting this material in DMF for 1 hour with excess PNA (sequence: NH2-Glu-GTGCTCATGGTG-CONH2, where Glu is a glutamate amino-acid residue and the central block represents nucleic-acid bases). The PNA-derivatized nanofabric is transferred to water and dispersed in 0.5% aqueous sodium dodecyl sulphate. To examine DNA hybridization to this modified nanofabric, fragments of double-stranded DNA with 12-base-pair, single-stranded "sticky" ends that were complementary to the PNA sequence were used. These fragments were produced by cutting double-stranded DNA with restriction enzymes and ligating the products to single-stranded oligonucleotides. This sticky DNA was hybridized to the PNA-nanofabric in water, deposited on freshly cleaved mica with 5 mM $MgCl_2$. The surface was rinsed and dried. Atomic-force micrographs of the DNA/PNA-nanofabric hybrids may then be recorded. The antisense properties of this derivatized complex may be exploited in biological applications, for example in biosensors.

These methods allow appreciable and measurable functionalization of nanotubes with specific moieties or sensing agents added directly through covalent bonding. In effect, the functionalized nanotube becomes a reactive chemical itself and further chemistry can be performed to yield such diverse species as nanotubes with nanocrystals and inorganic compounds. Further details may be found in the following references, the entire contents of which are incorporated herein by reference: S. Baneijee et al., "Functionalization of Carbon Nanotubes with a Metal-Containing Molecular Complex," *Nano Lett.*, vol. 2, no. 1, pp. 49-53 (2002); S. Banerjee et al., "Synthesis and Characterization of Carbon Nanotube-Nanocrystal Heterostructures," *Nano Lett.*, vol. 2, no. 3, pp. 195-200 (2002); S. Banerjee et al., "Structural Characterization, Optical Properties, and Improved Solubility of Carbon Nanotubes Functionalized with Wilkinson's Catalyst," *J. Am. Chem. Soc.*, vol. 124, no. 30, pp. 8490-48 (2002). These functionalized-nanotube building blocks can be modified using the wealth of available chemistries to decorate them with groups and moieties necessary to sense nearly any chemical or biological agent desired.

As is the case with non-covalently functionalized, covalently functionalized nanotubes may be used in three ways to create nanofabric sensor elements. The nanotubes may be functionalized separately and applied to a substrate, for example, by using a spin coating method or other method of application. In other embodiments, the nanofabric may be applied to a substrate and subsequently covalently functionalized before patterning. In yet other embodiments, the nanofabric may be functionalized after creation and patterning of the nanofabric. Each of these three methods lends itself to creation of a nanofabric comprising one or more types of functionalized nanotubes in the presence or absence of pristine nanotubes, depending upon the sensor application desired. Upon successful generation of a source of nanotubes containing the proper set of functional moieties, a nanosensor system can be fabricated using various methods and light detection schemes can be used with such nanosensor fabric elements.

4. Hybrid

A fourth type of nanofabric sensor element uses a mixture of two or three of the previously mentioned types. By using such a mixture, a hybrid nanofabric sensor element is created with multiple binding-site types potentially able to detect multiple analytes and analyte types. Many different possible compositions of surface-functionalized nanotubes can be created before nanotubes are applied to the substrate, thereby allowing for a mixture of sensing components which can simultaneously screen for discrete analytes.

Methods of Making Exemplary Embodiments

FIGS. 4A-M illustrate various intermediate structures created during an exemplary method of creating exemplary nanofabric sensor elements like those of FIG. 3A or, with some modification.

A silicon wafer substrate 402 with an insulating or oxide layer 404 is provided. Alternatively, the substrate may be made from any material suitable for use with lithographic etching and electronics, and the oxide layer can be any suitable insulator. The oxide layer 404 has a top surface 404'. A nitride layer 406 (or any suitable insulator) is deposited on the surface of intermediate structure 404, thereby forming intermediate structure 408 of FIG. 4A. A non-limiting example of nitride thickness is approximately 20 nm for 0.18 micron ground rule (GR). The nitride thickness may vary depending on the ground rule of the desired final product. The oxide layer 404 is preferably a few nanometers in thickness, but could be as much as 1 µm thick, or far thicker depending on the ultimate use of the sensor.

Nitride layer 406 is then patterned and etched to generate cavities corresponding in size and shape to gap region 412. Remaining nitride layer 414 is left in the area around such a cavity, thus forming intermediate structure 416 of FIG. 4B.

Figure 4A:
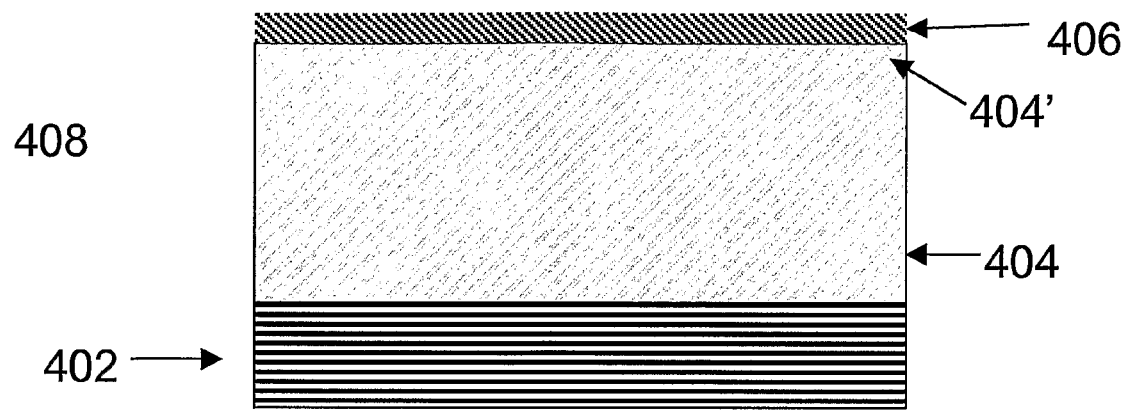
FIGS. 4A-M and 4L'-M' illustrate structures formed during steps in a method of making horizontally oriented nanofabric sensor elements.
Figure 4B:
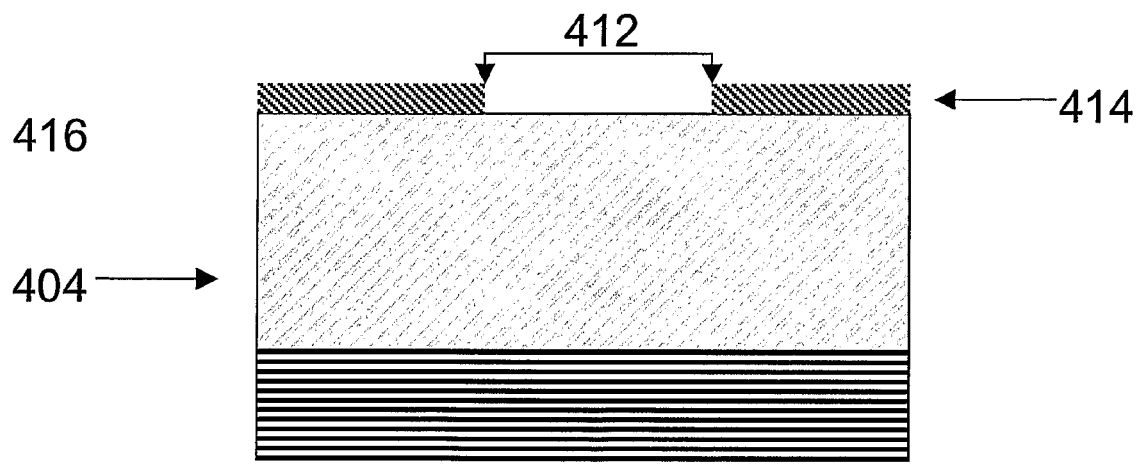
Figure 4C:
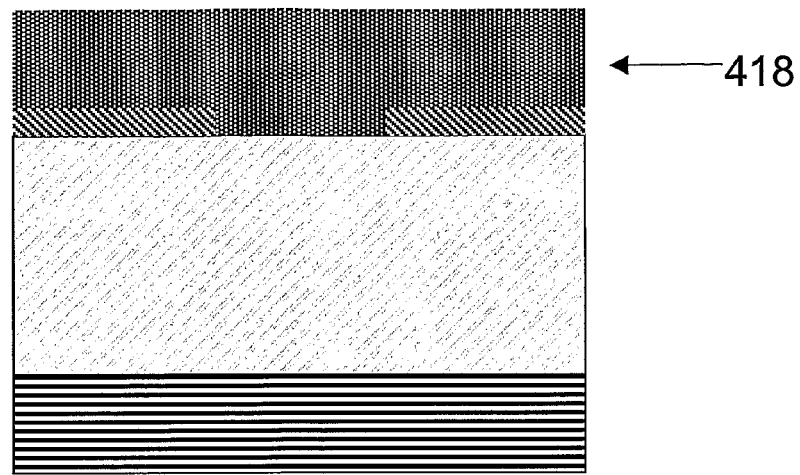

Sacrificial layer 418 is deposited on the surface of intermediate structure 416, forming intermediate structure 420 of FIG. 4C. A non-limiting example of the material from which sacrificial layer 418 can be made is polysilicon. However, any appropriate material selectively etchable (when necessary) over other materials of certain embodiments of the present invention can be used, such as, but not limited too, amorphous-Silicon, Al, Mo, Ge, Alumina, Ti, Pd, photoresists, polymers, or any combination of the above. A non-limiting parameter for the thickness of sacrificial layer 418 is that it be on the order of 100 to 200 nm.

Figure 4D:
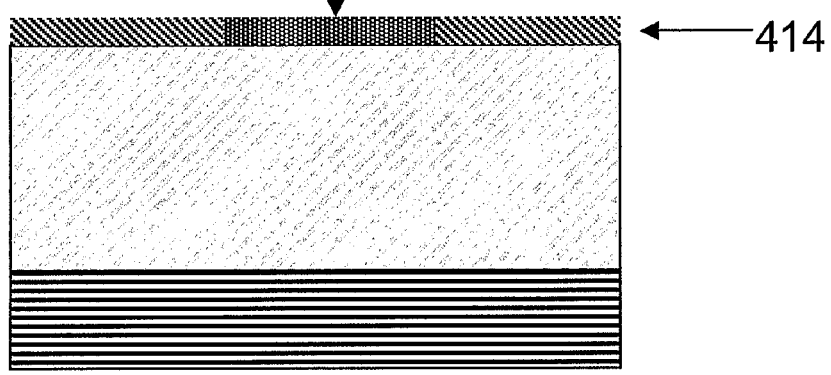

The top surface of intermediate structure 420 is planarized such that the surface of the remaining polysilicon layer 422 is substantially level with the top surface of remaining nitride layer 414, thus forming intermediate structure 424 of FIG. 4D.

Figure 4E:
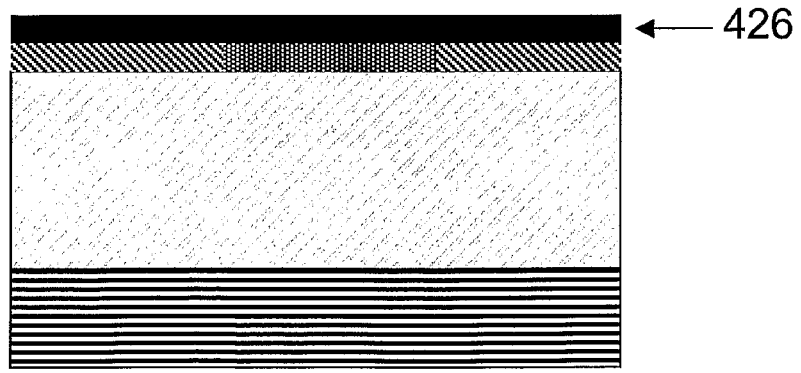

A nanotube fabric 426 is applied to, or formed on, the surface of intermediate structure 424, thus forming intermediate structure 428 of FIG. 4E. Non-limiting methods of applying such a fabric are spin coating, aerosol application, dipping, or chemical vapor deposition as described in the references listed and incorporated above.

Figure 4F:
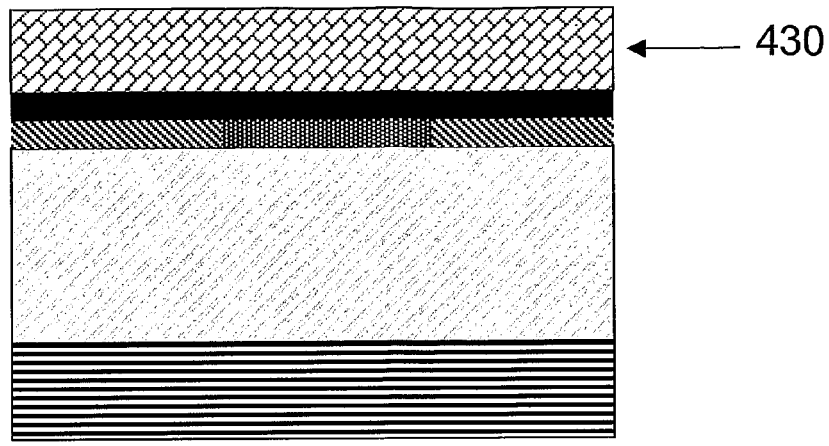

Resist layer 430 is applied to the surface of intermediate structure 428, forming intermediate structure 432 of FIG. 4F.

Figure 4G:
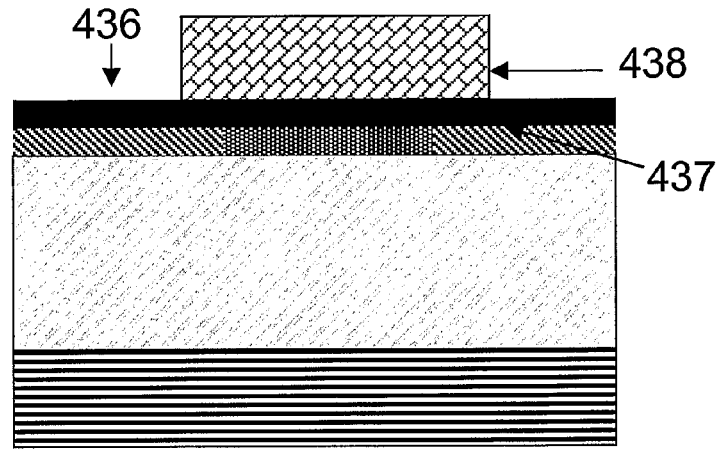
Figure 4H:
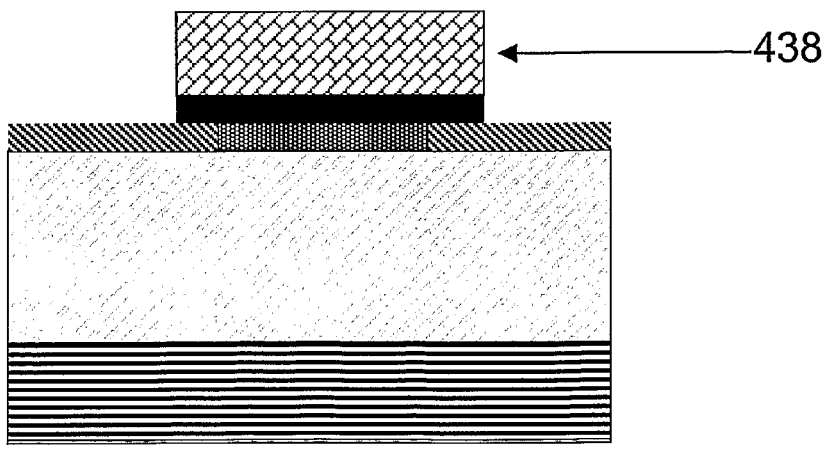

As indicated in FIG. 4G, a nanotube fabric region 437 (indicated by dashed lines) larger than gap region 412 (see FIG. 4E) is patterned by first lithographically patterning resist layer 430, forming intermediate structure 434 with exposed nanofabric portions 436 and patterned resist layer 438. Exposed nanotube fabric 436 is then removed, forming intermediate structure 440 of FIG. 4H. A non-limiting method of patterning the nanotube fabric is by plasma ashing.

Figure 4I:
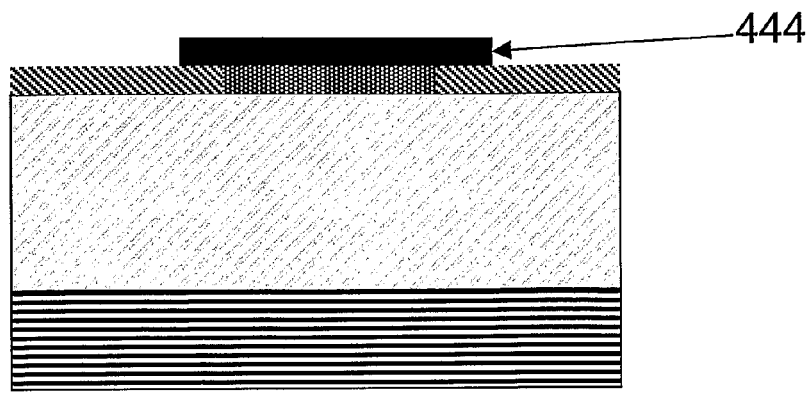

Patterned resist layer 438 is removed using any appropriate method, such as stripping, forming intermediate structure 442 of FIG. 4I. Structure 442 has patterned nanotube fabric 444, corresponding essentially to nanotube fabric region 437 in FIG. 4G.

Figure 4J:
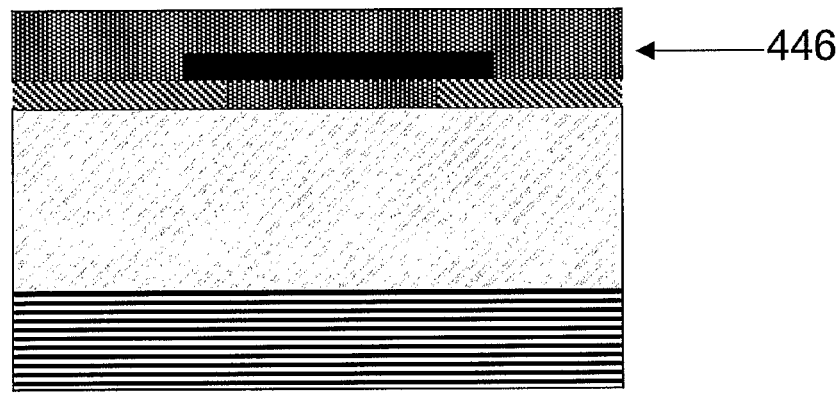
Figure 4K:
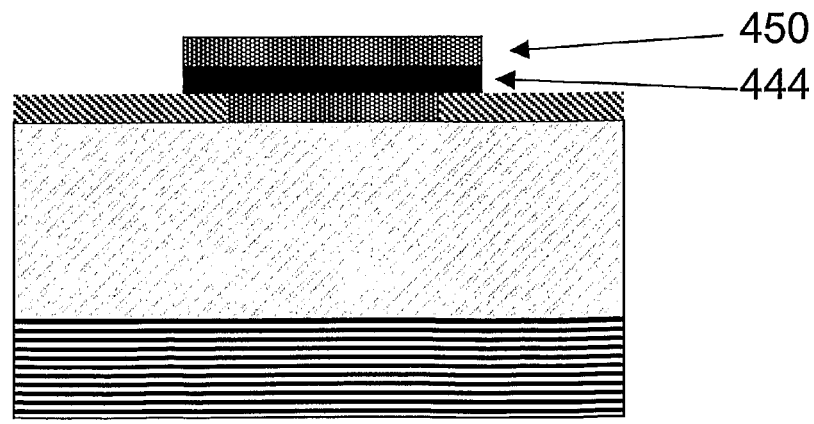
Figure 4L:
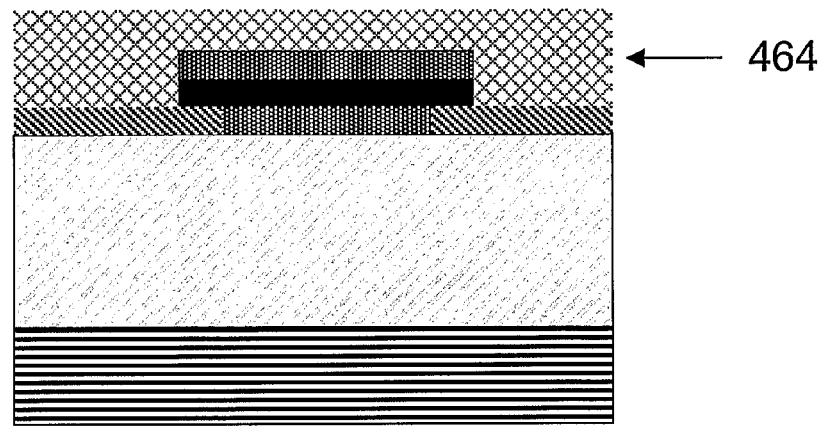
Figure 4M:
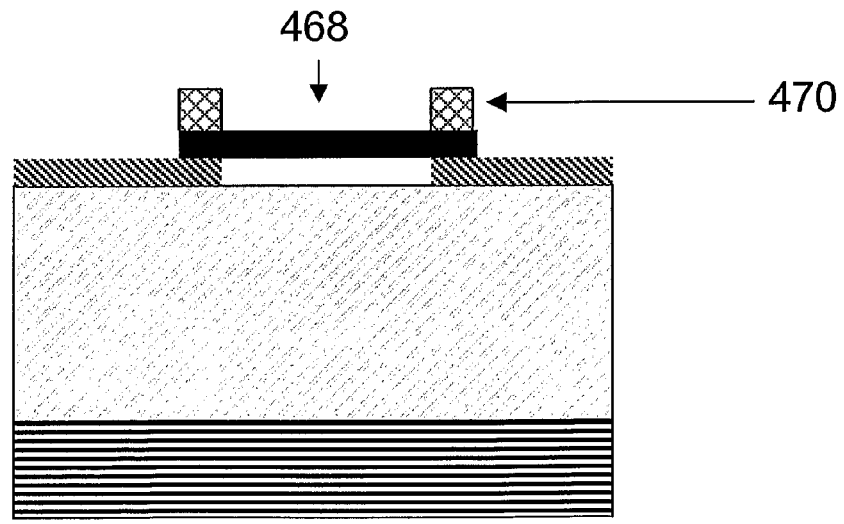

Polysilicon layer 446 is deposited over the surface of intermediate structure 442 to form intermediate structure 448 of FIG. 4J. A non-limiting range for the thickness of polysilicon layer 446 is between about 20 to 50 nm. Polysilicon layer 446 is patterned, for example, by etching to form intermediate structure 452 of FIG. 4K, which has remaining polysilicon layer portion 450 over nanotube sensor gap region 412. Remaining polysilicon layer portion 460 is larger than nanotube sensor gap region 412 and is the same size or larger than the underlying patterned nanotube fabric 444.

Metal layer 464 is deposited over structure 452, thus forming intermediate structure 466. The metal 464 is patterned, e.g. lithographically, (steps not shown) and polysilicon 422 and 450 is removed, e.g. by etching thus forming structure 4M. Metal layer 464 may be deposited without patterning by any appropriate means including sputtering or evaporation.

In cases where the sensor is to be in an encapsulated space and the nonlinearly generated light must pass through a translucent or transparent material, e.g. silicon crystal or ITO, then crystal 464' may be disposed on intermediate structure 452, thus forming structure 466', as shown in structure 4L'. Polysilicon 422 and 450 is removed, e.g., by etching, thus forming structure 468 having a suspended fabric under a crystal covering 464', as shown in structure 4M'.

The total concentration of binding moieties can be determined by using streptavidin that is bound with gold particles. The particles for a given area of nanofabric can be counted by SEM or AFM to determine the order of magnitude sensitivity available within a particular device. Since such derivatization can take place over an entire wafer, it is straightforward to fabricate nanofabric sensor elements with a very narrow range of characteristic binding concentrations.

The methods of fabrication for the nanofabric sensor elements of various embodiments of the present invention do not require the use of substrates that can withstand CVD temperatures. However, such substrates may also be used. Sensors of preferred embodiments are typically include nanotube fabrics with redundant conducting nanotubes. These fabrics may be created via CVD, or by room-temperature operations as described herein and in the incorporated patent references. In such a redundant sensor, if one sensing nanotube breaks, the device would remain operable because of the redundant conductive elements in each sensor. Because the nanosensor described herein can be fabricated at room temperature, the use of nearly any substrate, including highly flexible materials and plastics is possible.

Nanofabric sensor elements according to certain embodiments can be readily manufactured using standard techniques found in the semiconductor industry such as spin coating and photolithography. The feature size of each nanofabric sensor element can be determined by photolithography or by deposition. Because such standard techniques are used in the construction of the nanofabric sensor elements, the overall cost, yield, and array size can be larger than sensors created by other known techniques. Nanofabric sensor elements can also be used in massive parallel arrays and can be multiplexed using standard CMOS-compatible sense amplifiers and control logic.

Nanofabric sensor elements may also be compatible with high-resolution contact printing methods. See H. Li. et al., "High-resolution Printing with Dendrimers," *Nano Lett.*, vol. 2, no. 4, pp. 347-49 (2002), the entire contents of which are incorporated herein by reference. Patterned nanofabrics may be created on a substrate (as described below and in the incorporated patent references), and those patterned nanotubes may be transferred via an appropriate contact printing method to a second substrate. Parameters such as solubility and binding affinity are important factors to be considered in selecting suitable substrates. Alternatively, functionalized, patterned nanotubes may be transferred in the same manner. And still another alternative that utilizes contact printing technology is the application of patterns of functionalization agent to specific, defined regions on patterned nanofabric—e.g., on different nanofabric sensor elements.

Nanofabric sensor element can be produced on surfaces that can withstand CVD temperatures and also on surfaces that may not withstand such a harsh environment —e.g., when spin coating or aerosol application methods are used to create the nanofabric.

As stated above, the nanotubes of the nanofabric may be derivatized or functionalized prior to formation of the nanofabric, subsequent to the formation of the fabric, or subsequent to the patterning of the fabric. In the latter case, for example, the three-dimensional structure might not be completely sealed but might instead have open channels whereby the nanofabric could be subjected to a derivatizing or functionalizing agent.

The devices and articles shown and described in the preceding embodiments are given for illustrative purposes only, and other techniques may be used to produce the same or equivalents thereof. Furthermore, the articles shown may be modified by the substitution of other types of materials or the use of different geometries. For example, as described above, rather than using metallic electrodes, some embodiments of the present invention may employ conductive interconnects made from, or comprising, nanotubes.

There are other electrode connection locations and geometries possible that one skilled in the art would know to create.

In order to deliver samples to be examined by the sensor, a microfluidic delivery system may be utilized. Samples of blood, body fluids, chemicals, and the like may be injected or fed into a microfluidic delivery system. Such a system could then move material through a system of microfluidic capillaries and pumps to the sensor site. See, e.g., PCT publication WO 00/62931, "The Use of Microfluidic systems in the Electrochemical Detection of Target Analytes", the entire contents of which are incorporated herein by reference.

Figure 5:
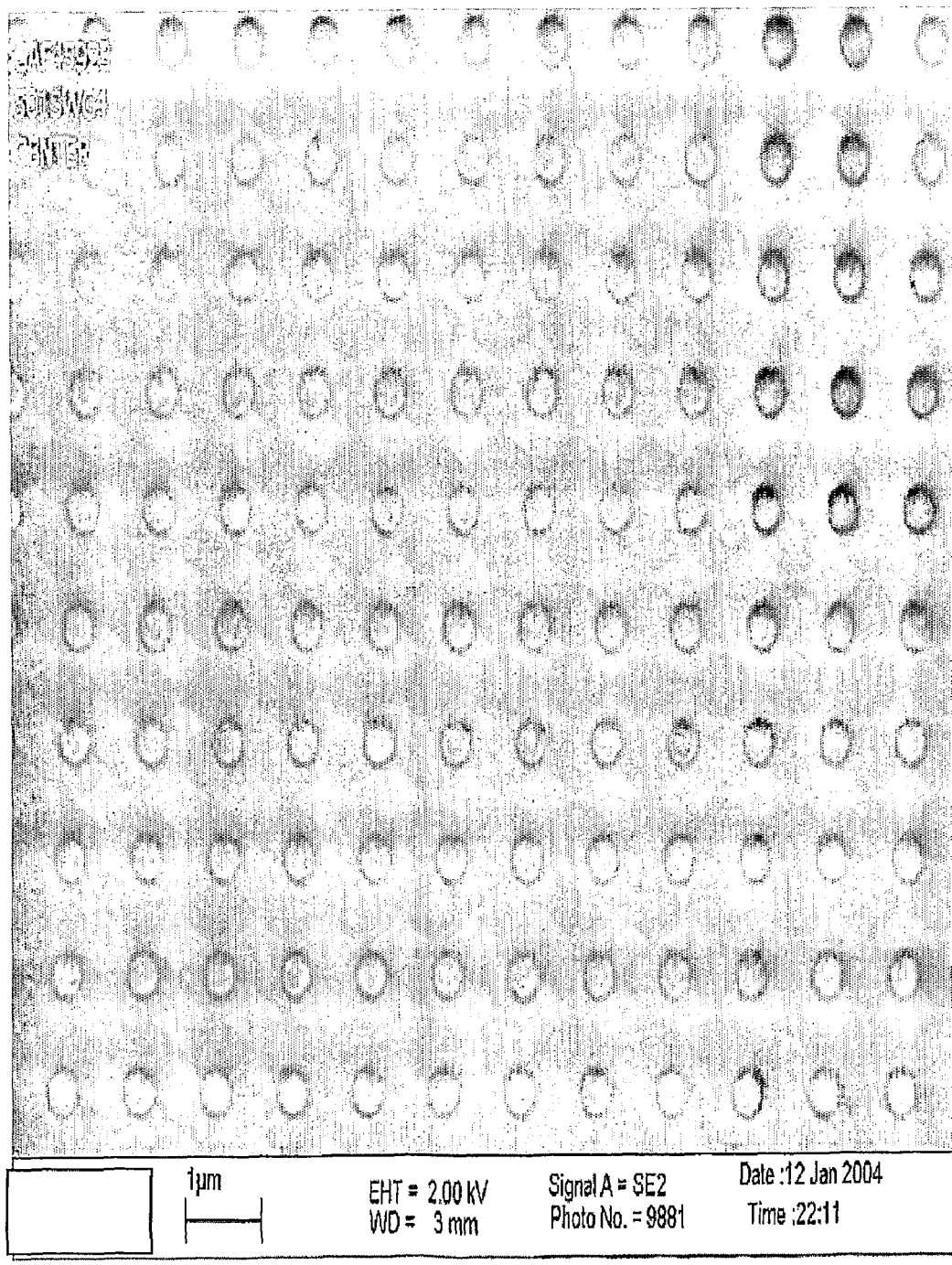
FIG. 5 illustrates a plan view of one possible structure for a large-scale array of addressable nanofabric sensor elements.

Some of the advantages of the nanofabric sensor elements according to certain embodiments include an ability to implement large-scale application and integration. This is facilitated by having CMOS-compatible manufacturing processes. FIG. 5 illustrates the possibilities for a large-scale array of addressable nanofabric sensor elements by showing an array of contact holes in which sensor elements might be located.

Figure 6A:
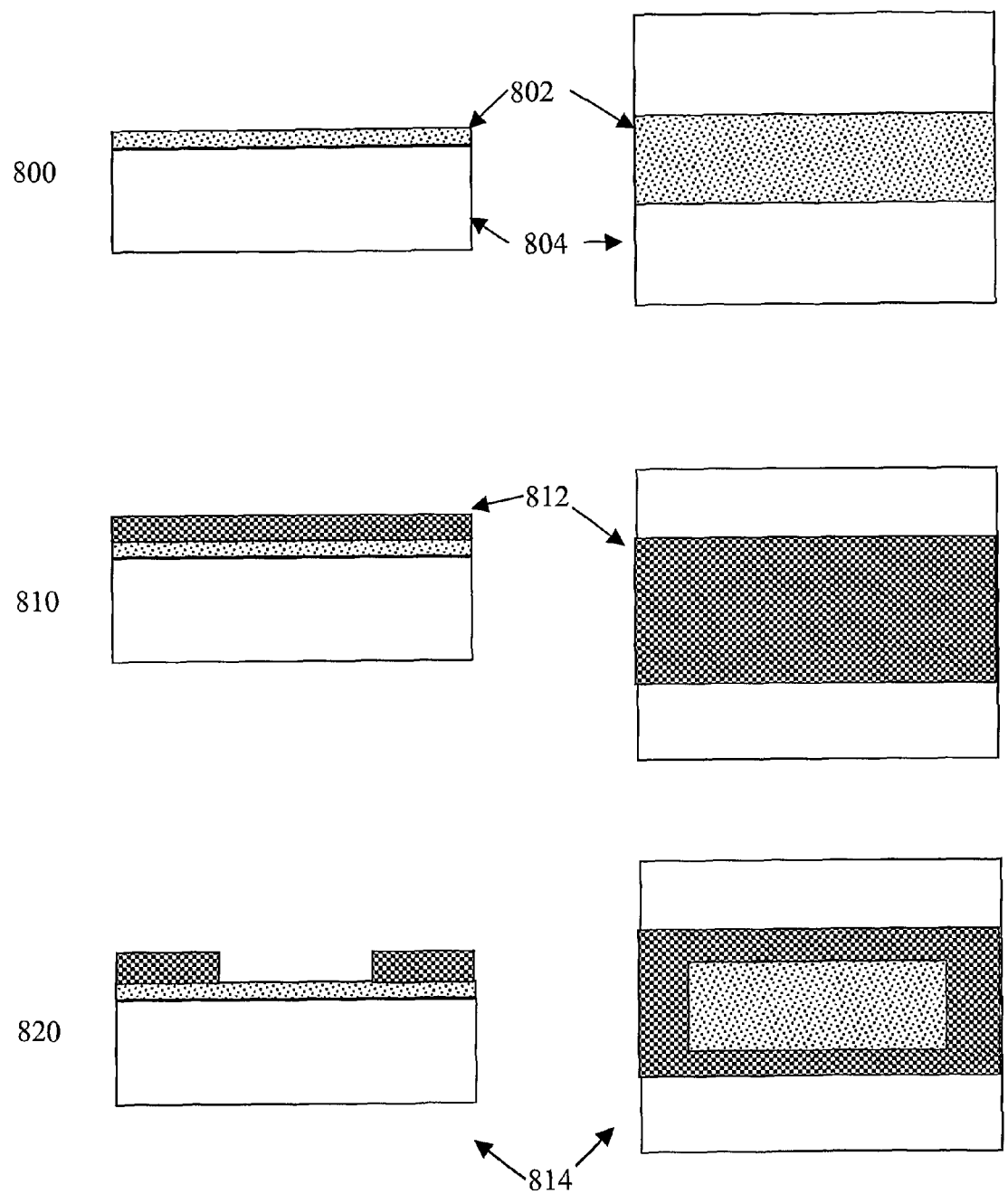
FIGS. 6A and 6B illustrate plan views and cross-sectional views of embodiments of nanofabric sensor elements.

FIG. 6A illustrates a plan view and a cross-sectional view of a nanofabric sensor element 814 having a framed portion of nanofabric 802, and a method for its creation. Such a framed fabric may be created by providing the nanofabric 802 on a substrate 804, as illustrated by intermediate structure 800, covering the fabric 802 with an appropriate covering material 812, as shown illustrated by intermediate structure 810, and lithographically patterning and removing a section of the covering material 812, leaving a "frame" of material around sensing fabric, as shown in intermediate structure 820. Such a strapping or clamping method is more fully described in U.S. patent application Ser. No. 10/776,059, Electromechanical Switches and Memory Cells Using Horizontally-Disposed Nanofabric Articles and Methods of Making Same, filed Feb. 11, 2004. The covering material may be conductive, and may act to alter the electrical properties of the entire patterned fabric, or it may be semiconducting or insulating.

The material of the strapping layer should be selectively etchable over nanofabric when used alone to open up a window of exposed fabric. The material of the covering layer may be selectively etchable over an intermediate layer disposed between the nanofabric and covering layer. The intermediate layer in this case may act as an etch stop when etching and patterning the covering layer.

Figure 6B:
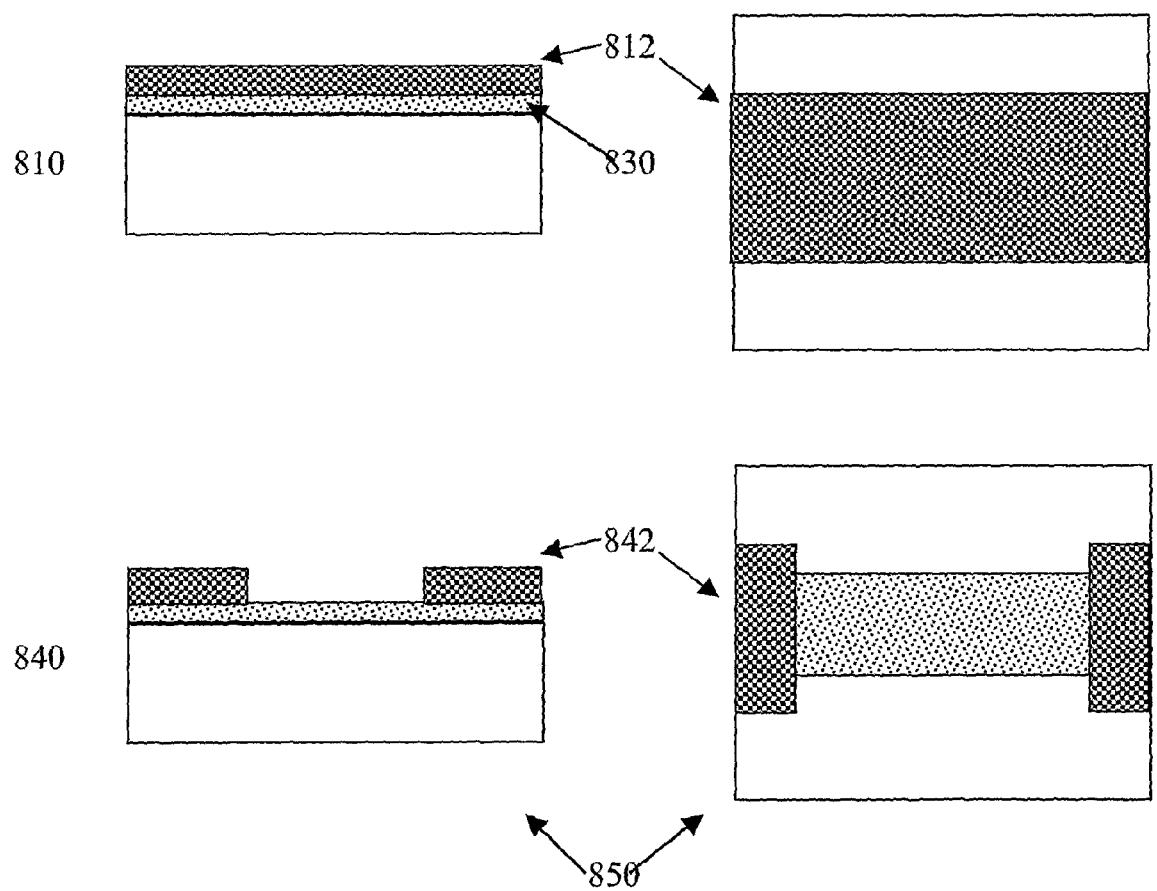

FIG. 6B illustrates a plan view and a cross-sectional view of a nanofabric sensor element 850 in which no frame is formed, but instead a set of disconnected sections of covering layer are formed over a nanotube fabric 830. Intermediate structure 810 is patterned to form clamping or pinning structures 842, as illustrated in intermediate structure 840.

Figure 7:
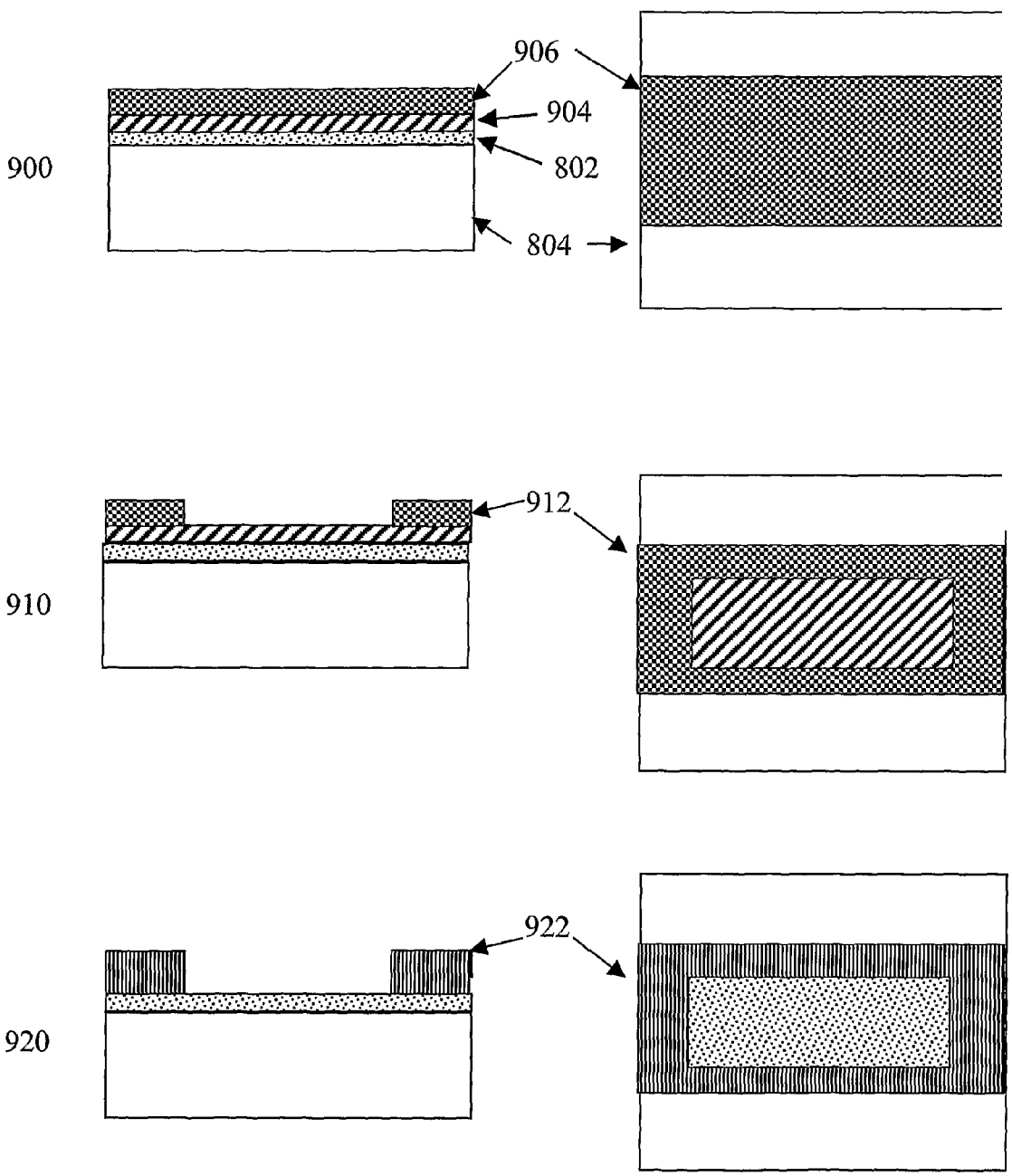
FIG. 7 illustrates plan views and cross-sectional views of embodiments of nanofabric sensor elements.

FIG. 7 illustrates structures formed in yet another method of patterning nanofabric sensor elements. Such a method involves a covering material 906 that is selectively etchable over an intermediate layer 904. Covering material 906 may preferably be a metal, and intermediate layer 904 may preferably be a semiconductor—e.g., silicon—but any materials suitable for the application will work. The intermediate layer 904 is disposed between the nanofabric 802 and covering layer 906. The intermediate layer 904 in this case may act as an etch stop when dry etching and patterning the covering layer 906. Intermediate structure 910 illustrates patterned covering layer 912 in the shape of a frame, however any pattern will work depending on the requirements of the final product. Intermediate structure 910 is subjected to an annealing step whereby covering layer 912 and intermediate layer 904 form a conducting composite layer 922—e.g., a metal silicide—permitting creation of structure 920. Such a composite layer can act as pinning or clamping structure or other contact or addressing element, depending on the use of the final products.

Other Embodiments

While the embodiments described above generally relate to nonlinear optical effects in which the CNT fabric generates light at a different frequency ($\omega_2$) than with which it is irradiated ($\omega_1$), in general the CNT fabric may have one or more other kinds of nonlinear responses. For example, the CNT fabric may respond to the electromagnetic radiation at $\omega_1$ by shifting or modifying a frequency, phase, and/or focusing characteristic of the radiation at $\omega_1$, and this shift or modification is measured by an optical detector.

Besides carbon nanotubes, other materials with nonlinear optical properties could be envisioned. As one example, a nanosensing fabric may be made entirely of carbon nanotubes, or it may be made from nanowires of various composition—e.g., silicon nanowires—or the fabric might be a composite of nanotubes and nanowires. Further details on the creation of nanowires and composite fabrics may be found in the incorporated patent references, such as in U.S. patent application No. 10/936,119, entitled "Patterned Nanoscopic Articles and Methods of Making the Same."

Fluid samples delivered to a sensor element for analyte detection can include both liquids and gases, and may include analytes in a variety of forms—for example, as part of particulate matter suspended in the fluid.

Further, certain of the above aspects, such as the hybrid circuits, are applicable to individual nanotubes (e.g., using directed growth techniques, etc.) or to nanotube ribbons. As used herein, phrases such as "collection of nanostructures" or "collection of nanotubes" each generally encompass a number of nanostructures or nanotubes, respectively, and potentially other matter, without regard to such considerations as whether any particular constituent or constituents of the collection have a special quality or distinctiveness, or are arranged in a particular way.

The term "functionalization," as used herein, generally includes both covalent and non-covalent modifications of nanotubes whereas the term "derivatization" signifies the covalent modification of nanotubes. Hence, functionalization may in certain instances involve non-covalent transformation of the surface of a nanotube into a form with different functional groups or moieties, and, for example, is meant to encompass any alteration, or addition, to a nanotube or nanotube surface—including covalent derivatization—that creates a product with different physical or electrical characteristics. Derivatization is indicative of a covalent alteration of the chemical structure of one or more nanotubes, or a portion thereof. In both circumstances, the process can be controlled such that electrical properties of nanotubes may be substantially retained. Functional groups can include inorganic atoms and molecules as well as organic molecules. Significant biological functional groups include peptides, nucleic acids, antigens (including polypeptide and non-polypeptide antigens) as well as peptide nucleic acids.

The following commonly-owned patent references, referred to herein as "incorporated patent references," describe various techniques for creating nanotube elements (nanotube fabric articles and switches), e.g., creating and patterning nanotube fabrics, and are incorporated herein by reference in their entireties:

U.S. patent application Ser. No. 09/915,093, Electromechanical Memory Array Using Nanotube Ribbons and Method for Making Same, filed Jul. 25, 2001, now U.S. Pat. No. 6,919,592;

U.S. patent application Ser. No. 09/915,173, Electromechanical Memory Having Cell Selection Circuitry Constructed with Nanotube Technology, filed Jul. 25, 2001, now U.S. Pat. No. 6,643,165;

U.S. patent application Ser. No. 09/915,095, Hybrid Circuit Having Nanotube Electromechanical Memory, filed Jul. 25, 2001, now U.S. Pat. No. 6,574,130;

U.S. patent application Ser. No. 10/033,323, Electromechanical Three-Trace Junction Devices, filed Dec. 28, 2001 now U.S. Pat. No. 6,911,682;

U.S. patent application Ser. No. 10/802,900, Electromechanical Three-Trace Junction Devices, filed Mar. 17, 2004;

U.S. patent application Ser. No. 10/033,032, Methods of Making Electromechanical Three-Trace Junction Devices, filed Dec. 28, 2001, now U.S. Pat. No. 6,784,028;

U.S. patent application Ser. No. 10/128,118, Nanotube Films and Articles, filed Apr. 23, 2002, now U.S. Pat. No. 6,706,402;

U.S. patent application Ser. No. 10/128,117, Methods of Nanotube Films and Articles, filed Apr. 23, 2002 now U.S. Pat. No. 6,835,591;

U.S. patent application Ser. No. 10/864,186, Non-Volatile Electromechanical Field Effect Devices and Circuits Using Same and Methods of Forming Same, filed Jun. 9, 2004, now U.S. Patent Publication No. 2005/0062035;

U.S. patent application Ser. No. 10/341,005, Methods of Making Carbon Nanotube Films, Layers, Fabrics, Ribbons, Elements and Articles, filed Jan. 13, 2003;

U.S. patent application Ser. No. 10/341,055, Methods of Using Thin Metal Layers To Make Carbon Nanotube Films, Layers, Fabrics, Ribbons, Elements and Articles, filed Jan. 13, 2003;

U.S. patent application Ser. No. 10/341,054, Methods of Using Pre-formed Nanotube Films, Layers, Fabrics, Ribbons, Elements and Articles, filed Jan. 13, 2003;

U.S. patent application Ser. No. 10/341,130, Carbon Nanotube Films, Layers, Fabrics, Ribbons, Elements and Articles, filed Jan. 13, 2003;

U.S. patent application Ser. No. 10/776,059, Electromechanical Switches and Memory Cells Using Horizontally-Disposed Nanofabric Articles and Methods of Making Same, filed Feb. 11, 2004;

U.S. patent application Ser. No. 10/776,572, Electromechanical Switches and Memory Cells Using Vertically-Disposed Nanofabric Articles and Methods of Making the Same, filed Feb. 11, 2004 now U.S. Pat. No. 6,924,538;

U.S. patent application Ser. No. 10/917,794, Nanotube-Based Switching Element, filed Aug. 13, 2004;

U.S. patent application Ser. No. 10/918,085, Nanotube-Based Switching Elements With Multiple Controls, filed Aug. 13, 2004;

U.S. patent application Ser. No. 10/936,119, Patterned Nanoscopic Articles and Methods of Making the Same, filed Sep. 8, 2004, now U.S. Patent Publication No. 2005/0128788; and U.S. patent application Ser. No. 11/398,126, Nanotube Articles with Adjustable Conductivity and Methods of Making the Same, filed Apr. 5, 2006.

It will be further appreciated that the scope of the present invention is not limited by the above-described embodiments, but rather is defined by the appended claims, and that these claims will encompass modifications of and improvements to what has been described.

What is claimed is:

1. A system for sensing the presence of an analyte in a fluid, the system comprising:
   a nanotube sensor element comprising a plurality of nanotubes and positioned for exposure to a fluid;
   an optical source capable of generating optical radiation, the radiation having a source frequency and a fluence selected to generate a nonlinear optical response by the nanotube sensor element;
   an optical detector capable of measuring the nonlinear optical response by the nanotube sensor element; and
   logic in electrical communication with the optical detector to sense the presence of an analyte in the fluid based on the nonlinear optical response measured by the optical detector;
   wherein the nanotube sensor element comprises supports defining a gap over which at least a portion of the plurality of nanotubes is suspended.

2. The system of claim 1, wherein the nanotube sensor element comprises a nonwoven fabric of nanotubes.

3. The system of claim 1, wherein the nonlinear optical response of the nanotube sensor element comprises the nanotube sensor element radiating optical energy at a different frequency than the source frequency.

4. The system of claim 3, wherein the nonlinear optical response of the nanotube sensor element comprises radiation at the third harmonic of the source frequency.

5. The system of claim 3, wherein attachment of the analyte to the nanotube sensor element changes the nonlinear optical response of the nanotube sensor element.

6. The system of claim 5, wherein attachment of the analyte to the nanotube sensor element causes a charge transfer between the nanotube sensor element and the analyte.

7. The system of claim 6, wherein the charge transfer changes the nonlinear optical response of the nanotube sensor element.

8. The system of claim 5, wherein the logic is capable of determining the change in the nonlinear optical response of the nanotube sensor element caused by attachment of the analyte and thus sensing the presence of the analyte.

9. The system of claim 5, wherein the change in the nonlinear response of the nanotube sensor element comprises a change in frequency of optical energy radiated by the nanotube sensor element.

10. The system of claim 9, wherein the optical detector detects the change in frequency of optical energy radiated by the nanotube sensor element.

11. The system of claim 1, wherein the nanotubes of the nanotube sensor element comprise pristine nanotubes.

12. The system of claim 1, wherein the nanotubes of the nanotube sensor element comprise nanotubes that are functionalized with analyte-specific molecules.

13. The system of claim 1, wherein the nanotubes of the nanotube sensor element comprise nanotubes that are derivitized with analyte-specific molecules.

14. The system of claim 1, wherein the nanotubes of the nanotube sensor element comprise nanotubes that are functionalized with a nonlinear material.

15. The system of claim 14, wherein the nonlinear material causes a change in the nonlinear optical response of the nanotube sensor element.

16. The system of claim 15, wherein the change in the nonlinear optical response comprises a change in frequency of optical energy radiated by the nanotube sensor element.

17. The system of claim 1, wherein the nanotubes of the nanotube sensor element are functionalized so as to have or increase an affinity for a particular analyte.

18. The system of claim 1, wherein the nanotubes of the nanotube sensor element are derivitized so as to have or to increase an affinity for a particular analyte.

19. The system of claim 1, wherein the nanotube sensor element is functionalized so as to have or to increase an affinity for multiple analytes.

20. The system of claim 1, wherein the nanotube sensor element is derivitized so as to have or to increase an affinity for multiple analytes.

21. The system of claim 1, further comprising material that clamps at least a portion of the plurality of nanotubes to at least a portion of the supports.

22. The system of claim 1, wherein the nanotube sensor element comprises a substrate on which the plurality of nanotubes is disposed.

23. The system of claim 1, wherein the optical source comprises a laser.

24. The system of claim 1, wherein the optical detector comprises a photodiode.

25. The system of claim 1, wherein the nanotube sensor element further comprises nanowires.

26. The system of claim 1, wherein the system is capable of sensing an analyte selected from the group consisting of a gaseous element, an airborne molecule, an organic molecule, an inorganic molecule, and a biological molecule.

27. The system of claim 26, wherein the biological molecule is selected from the group consisting of a peptide, a protein, and a nucleic acid.

28. The system of claim 1, wherein the nanotubes of the nanotube sensor element comprise substantially a monolayer of nanotubes.

* * * * *